United States Patent
Masters et al.

(10) Patent No.: US 8,465,537 B2
(45) Date of Patent: *Jun. 18, 2013

(54) ENCAPSULATED OR COATED STENT SYSTEMS

(75) Inventors: David B. Masters, Minneapolis, MN (US); Eric P. Berg, Plymouth, MN (US)

(73) Assignee: Gel-Del Technologies, Inc., St. Paul, MN (US)

( * ) Notice: Subject to any disclaimer, the term of this patent is extended or adjusted under 35 U.S.C. 154(b) by 146 days.

This patent is subject to a terminal disclaimer.

(21) Appl. No.: 10/871,946

(22) Filed: Jun. 17, 2004

(65) Prior Publication Data

US 2006/0167540 A1    Jul. 27, 2006

Related U.S. Application Data

(60) Provisional application No. 60/478,976, filed on Jun. 17, 2003.

(51) Int. Cl.
*A61F 2/06* (2006.01)

(52) U.S. Cl.
USPC ............................................................ 623/1.13

(58) Field of Classification Search
USPC .................. 623/1.16, 1.22, 1.13, 1.42, 1.46, 623/1.47, 1.48; 424/492; 606/1.47, 1.48; 514/9.3, 17.2, 54, 55, 56
See application file for complete search history.

(56) References Cited

U.S. PATENT DOCUMENTS

| | | | |
|---|---|---|---|
| 3,800,792 A | 4/1974 | McKnight | 602/50 |
| 3,996,934 A | 12/1976 | Zaffaroni | 424/434 |
| 4,060,081 A | 11/1977 | Yannas | 623/15.12 |
| 4,226,848 A | 10/1980 | Nagai | 514/772.1 |
| 4,250,163 A | 2/1981 | Nagai | 514/772.1 |
| 4,252,759 A | 2/1981 | Yannas | 264/86 |
| 4,280,954 A | 7/1981 | Yannas | 530/356 |
| 4,286,592 A | 9/1981 | Chandrasekaran | 424/448 |
| 4,292,299 A | 9/1981 | Suzuki | 424/435 |
| 4,347,234 A | 8/1982 | Wahlig | 424/426 |
| 4,350,629 A | 9/1982 | Yannas | 530/356 |
| 4,352,883 A | 10/1982 | Lim | 435/178 |
| 4,394,370 A | 7/1983 | Jefferies | 606/76 |
| 4,405,311 A | 9/1983 | Greatbatch | 604/20 |
| 4,418,691 A | 12/1983 | Yannas | 424/548 |

(Continued)

FOREIGN PATENT DOCUMENTS

| | | |
|---|---|---|
| CA | 1239755 | 8/1988 |
| CA | 1245527 | 11/1988 |

(Continued)

OTHER PUBLICATIONS

Handbook of Food Science, Technology and Engineering. Yiu, Hu H. (editor), 2006, CRC Press.*

(Continued)

*Primary Examiner* — Thomas McEvoy

(74) *Attorney, Agent, or Firm* — Patterson Thuente Pedersen, P.A.

(57) ABSTRACT

A stent system having zero or more inner stents inserted into an outer stent. The inner stents and outer stent are separated and/or encapsulated by a protein-based material of a protein matrix and/or a set biocoacervate, each one or more biocompatible proteins and one or more biocompatible solvents. The protein-based material may also include one or more carbohydrates and one or more pharmacologically active agents.

27 Claims, 11 Drawing Sheets

U.S. PATENT DOCUMENTS

| | | | |
|---|---|---|---|
| 4,438,253 A | 3/1984 | Casey et al. | 528/86 |
| 4,448,718 A | 5/1984 | Yannas | 530/356 |
| 4,458,678 A | 7/1984 | Yannas | 602/48 |
| 4,474,752 A | 10/1984 | Haslam | 424/78 |
| 4,505,266 A | 3/1985 | Yannas | 128/898 |
| 4,517,173 A | 5/1985 | Kizawa | 424/435 |
| 4,518,721 A | 5/1985 | Dhabhar | 523/120 |
| 4,522,753 A | 6/1985 | Yannas | 530/356 |
| 4,526,938 A | 7/1985 | Churchill et al. | 525/415 |
| 4,553,545 A * | 11/1985 | Maass et al. | 606/198 |
| 4,572,832 A | 2/1986 | Kigasawa | 514/772.1 |
| 4,596,574 A | 6/1986 | Urist | 424/422 |
| 4,600,533 A | 7/1986 | Chu | 530/356 |
| 4,652,441 A | 3/1987 | Okada et al. | 424/497 |
| 4,706,680 A | 11/1987 | Keusch | 600/392 |
| 4,713,243 A | 12/1987 | Schiraldi | 424/676 |
| 4,733,665 A | 3/1988 | Palmaz | 606/108 |
| 4,739,762 A | 4/1988 | Palmaz | 623/1.11 |
| 4,741,872 A | 5/1988 | De Luca | 264/4.7 |
| 4,780,450 A | 10/1988 | Sauk | 514/2 |
| 4,787,900 A | 11/1988 | Yannas | 600/36 |
| 4,800,882 A | 1/1989 | Gianturco | 606/194 |
| 4,801,299 A | 1/1989 | Brendel | 623/1 |
| 4,849,141 A | 7/1989 | Fujioka | 264/207 |
| 4,894,232 A | 1/1990 | Reul | 424/439 |
| 4,900,554 A | 2/1990 | Yanagibashi | 424/448 |
| 4,902,289 A | 2/1990 | Yannas | 623/1.47 |
| 4,907,336 A | 3/1990 | Gianturco | 29/515 |
| 4,915,948 A | 4/1990 | Gallopo | 424/435 |
| 4,917,161 A | 4/1990 | Townend | 131/352 |
| 4,947,840 A | 8/1990 | Yannas | 602/50 |
| 4,955,893 A | 9/1990 | Yannas | 606/154 |
| 4,959,217 A | 9/1990 | Sanders | 424/473 |
| 5,019,372 A | 5/1991 | Folkman | 424/422 |
| 5,035,706 A | 7/1991 | Gianturco et al. | 606/194 |
| 5,037,392 A | 8/1991 | Hillstead | 606/194 |
| 5,041,126 A | 8/1991 | Gianturco | 623/1.15 |
| 5,041,292 A | 8/1991 | Feijen | 424/484 |
| 5,100,669 A | 3/1992 | Hyon et al. | 424/426 |
| 5,102,417 A | 4/1992 | Palmaz | 606/195 |
| 5,137,729 A | 8/1992 | Kuroya | 424/435 |
| 5,147,385 A | 9/1992 | Beck et al. | 128/898 |
| 5,188,837 A | 2/1993 | Domb | 424/450 |
| 5,192,802 A | 3/1993 | Rencher | 514/535 |
| 5,282,824 A * | 2/1994 | Gianturco | 623/1.13 |
| 5,298,258 A | 3/1994 | Akemi | 424/484 |
| 5,314,915 A | 5/1994 | Rencher | 514/535 |
| 5,316,023 A | 5/1994 | Palmaz et al. | 128/898 |
| 5,324,261 A | 6/1994 | Amundson | 604/103.02 |
| 5,324,775 A | 6/1994 | Ree et al. | 525/54.2 |
| 5,330,768 A | 7/1994 | Park et al. | 424/501 |
| 5,385,606 A | 1/1995 | Kowanko | 106/156.3 |
| 5,418,222 A | 5/1995 | Song | 514/21 |
| 5,423,739 A | 6/1995 | Phipps | 604/20 |
| 5,431,921 A | 7/1995 | Thombre | 424/424 |
| 5,443,483 A | 8/1995 | Kirsch | 606/74 |
| 5,447,940 A | 9/1995 | Harvey | 514/310 |
| 5,487,895 A | 1/1996 | Dapper | 424/278.1 |
| 5,489,304 A | 2/1996 | Orgill | 128/898 |
| 5,510,077 A | 4/1996 | Dinh | 264/485 |
| 5,512,291 A * | 4/1996 | Li | 424/443 |
| 5,518,502 A | 5/1996 | Kaplan | 600/157 |
| 5,573,934 A | 11/1996 | Hubbell | 435/177 |
| 5,607,445 A * | 3/1997 | Summers | 623/1.22 |
| 5,642,749 A | 7/1997 | Perryman | 135/66 |
| 5,665,428 A | 9/1997 | Cha | 427/213.3 |
| 5,676,699 A | 10/1997 | Gogolewski | 623/16.11 |
| 5,700,478 A | 12/1997 | Biegajski et al. | 427/213 |
| 5,709,683 A | 1/1998 | Bagby | 606/61 |
| 5,716,411 A | 2/1998 | Orgill | 435/371 |
| RE35,748 E | 3/1998 | Luck | 514/2 |
| 5,741,670 A | 4/1998 | Goetinck | 435/69.1 |
| 5,759,582 A | 6/1998 | Leong | 424/492 |
| 5,773,019 A | 6/1998 | Ashton | 424/423 |
| 5,783,214 A | 7/1998 | Royer | 424/499 |
| 5,834,232 A | 11/1998 | Bishop | 435/68.1 |
| 5,879,713 A | 3/1999 | Roth | 424/489 |
| 5,948,427 A * | 9/1999 | Yamamoto et al. | 424/426 |
| 5,980,551 A * | 11/1999 | Summers et al. | 606/194 |
| 5,981,568 A | 11/1999 | Kunz et al. | |
| 6,004,943 A | 12/1999 | Shi | 514/44 R |
| 6,048,360 A * | 4/2000 | Khosravi et al. | 623/1.11 |
| 6,074,689 A | 6/2000 | Luck | 427/2.21 |
| 6,124,273 A | 9/2000 | Drohan | 514/55 |
| 6,129,705 A * | 10/2000 | Grantz | 604/103.02 |
| 6,179,834 B1 * | 1/2001 | Buysse et al. | 606/41 |
| 6,210,429 B1 * | 4/2001 | Vardi et al. | 623/1.11 |
| 6,248,110 B1 | 6/2001 | Reiley | 606/93 |
| 6,287,765 B1 | 9/2001 | Cubicciotti | 435/6 |
| 6,291,582 B1 | 9/2001 | Dordick | 525/54.1 |
| 6,342,250 B1 | 1/2002 | Masters | 424/484 |
| 6,371,988 B1 | 4/2002 | Pafford | 623/17.11 |
| 6,656,506 B1 * | 12/2003 | Wu et al. | 424/489 |
| 6,814,980 B2 * | 11/2004 | Levy et al. | 424/497 |
| 6,960,452 B2 | 11/2005 | Hubbell | 435/69.7 |
| 2001/0008636 A1 * | 7/2001 | Yamamoto et al. | 424/426 |
| 2001/0020086 A1 | 9/2001 | Hubbell | 530/322 |
| 2002/0028243 A1 * | 3/2002 | Masters | 424/484 |
| 2002/0052572 A1 * | 5/2002 | Franco et al. | 604/8 |
| 2002/0065553 A1 * | 5/2002 | Weber | 623/1.46 |
| 2003/0007991 A1 | 1/2003 | Masters | 424/400 |
| 2003/0028204 A1 * | 2/2003 | Li et al. | 606/152 |
| 2004/0002558 A1 | 1/2004 | McKay | 623/23 |
| 2005/0147690 A1 | 7/2005 | Masters | 424/489 |
| 2006/0210601 A1 * | 9/2006 | Yunoki et al. | 424/423 |

FOREIGN PATENT DOCUMENTS

| | | |
|---|---|---|
| CA | 2085255 | 12/1991 |
| CA | 2134997 | 11/1994 |
| CA | 2171047 | 3/1996 |
| CA | 2175722 | 5/1996 |
| CA | 2185740 | 9/1996 |
| CA | 2192520 | 12/1996 |
| CA | 2239775 | 6/1997 |
| CA | 2251129 | 11/1997 |
| CA | 2290806 | 12/1998 |
| EP | 0 224 934 B1 | 6/1987 |
| EP | 0258780 A2 | 8/1987 |
| EP | 0 485 210 A2 | 5/1992 |
| EP | 0 518 697 A2 | 12/1992 |
| EP | 0 567 234 A1 | 3/1993 |
| EP | 0 636 378 B1 | 7/1994 |
| WO | WO 93/24150 | 12/1993 |
| WO | WO 97/32543 | 9/1997 |
| WO | WO 97/32544 | 9/1997 |
| WO | 97/41899 A1 | 11/1997 |
| WO | WO 97/41803 | 11/1997 |
| WO | WO 99/32613 A1 | 7/1999 |
| WO | 99/38546 A1 | 8/1999 |
| WO | 99/49907 A1 | 10/1999 |
| WO | 01/19305 A1 | 3/2001 |
| WO | WO 01/66161 A1 | 9/2001 |
| WO | WO 0183522 A2 | 11/2001 |
| WO | WO 0187267 A1 | 11/2001 |

OTHER PUBLICATIONS

Polymeric Materials Encyclopedia. Salamone, J. C. (editor), 1996, CRC Press. (see p. 7451).*

Masters et al.; U.S. Appl. No. 10/929,117 entitled "Protein Biomaterials and Biocoacervates and Methods of Making and Using Thereof" files Aug. 26, 2004.*

US 5,679,669, 10/1997, Colvard, (withdrawn).

Anderson "Morphology and Primary Crystal Structure of a Silk-like Protein Polymer Synthesized by Genetically Engineered *Escherichia Coli* Bacteria", *Biopolymers*, New York, NY, vol. 34, No. 8, Aug. 1, 1994, pp. 1049-1058.

Bradley "Some mechanical property considerations of reconstituted collagen for drug release supports", *Biomaterials, Medical Devices, and Artificial Organs*, 1997, vol. 5, No. 2, pp. 159-175.

Bredenberg et al., "In-vitro evaluation of bioadhesion in particulate systems and possible improvement using interactive mixtures." *Pharmacy and Pharmacology* 2003:55:169-177.

Cappello "In situ self-assembling protein polymer gel systems for administration, delivery and release of drugs", *Journal of controlled Release, Elsevier*, Amsterdam, NL, vol. 53, No. 1-3, Apr. 30, 1998, pp. 105-117.

Ferrari "Biosynthesis of Protein Polymers", *Protein-Based Materials*, 1997, pp. 37-60.
Foscolo "Full Length article" Biofutur. Le Mensuel Europeen DE Biotechnology, Lavoisier, Cachan, FR vol. 1997 (Oct. 1997), pp. 14-17.
Lee, J. Controlled Release, 2, 227 (1985).
Masters, Letter to Joseph Cappello, Jul. 1, 1996.
Masters, Improvements in Perineural Local Anesthetic Block, Abstract, CRISP—Computer Retrieval of Information on Scientific Projects, printed Sep. 22, 1998.
Mellon et al., "Water Adsorption of Proteins. IV. Effect of Physical Structure." *Journal of the American Chemical Society* 1949:71;2761-2764.
Morrione; "The Formation of Collagen Fibers by the Action of Heparin on Soluble Collagen: An Electron Microscope Study"; 1952; *J. Exp. Med.*; 96(2): 107-14.
Nomura, et al.; "Preparation and Some Properties of Type I Collagen from Fish Scales"; 1996; *Biosci. Biotech. Biochem.*; 60(12): 2092-2094.
Puri et al., "Adjuvancy enhancement of muramyl dipeptide by modulatin its release from a physico-chemically modified matrix of ovalbumin micorpsheres I. In vitro characterization." *Journal of Controlled Release* 2000:69;63-67.
Sammi Gelatin; http://sammi-getalin.com/em2.html; 2003; accessed online Jul. 20, 2009.
Http://www.merriam-webster.com/dictionary/binding (accessed Jan. 24, 2009).
European Patent Office Office Action dated Jul. 25, 2012, 5 pages.
AAPS: Annual Meeting & Exposition, *Symposia Abstracts & Biographies*, Boston, MA, Nov. 2, 1997, pp. 25-27.
Abbott, et al., *Vascular Grafts: Characteristics and Routine Selection of Prostheses*, Vascular Surgery, a Comprehensive Review, 5$^{th}$ Edition.
Abstracts, *Eighth International Symposium on Recent Advances in Drug Delivery Systems*, Feb. 24, 1997, Salt Lake City, UT, pp. 36-39, 138-140.
*American Red Cross Open to Partners for New Fibrin Sealant*, Genetic Engineering News, Mar. 1995, p. 30.
Anderson, *Characterization of Silk-like Proteins and Processing for Biomedical Applications*, Protein-Based Materials, 1997, pp. 371-423.
*The Biological Production of Protein Polymers and Their Use*, Trends in Biotechnology, Nov. 1990, vol. 8, No. 11.
Cappello, et al., *Microbial Production of Structural Polymers*, (ed. Mobley), 1994 Carl Hanser Verlag, Munich, pp. 35-92.
Cappello, et al., *Genetic Engineering of Structural Protein Polymers*, Biotechnology Progress, 1990, pp. 198-202.
Cappello, *Protein Engineering for Biomaterials Applications*, Current Opinion in Structural Biology, 1992, 2:582-586.
Caruana, *New Drugs Spur Novel Delivery Systems*, Chemical Engineering Progress, Jul. 1997, pp. 15-19.
Choi, et al. Implantation Biology: The Host Response and Biomedical Devices. *The Effect of Biomaterials on the Host*, CRC Press, Boca Raton 405 pages. 1994. Chapter 3, pp. 39-53.
Chvapil, et al., *Some Chemical and Biological Characteristics of a New Collagen-Polymer\* Compound Material*, J. Biomed. Mater. Res. vol. 3, pp. 315-331 (1969).
Davis, et al., *Chemically Cross-Linked Albumin Microspheres for the Controlled Release of Incorporated Rose Bengal After Instramuscular Injection Into Rabbits*, Journal of Controlled Release, 4 (1987) 293-302.
Dickinson, et al., *Biodegradation of a poly(a-amino acid) hydrogel. I.* In vivo, Journal of Biomedical Materials Research, vol. 15, 577-589 (1981).
Drug Delivery Systems (Program), Feb. 1998, San Francisco.
Dunn, et al., *Biomaterials Used in Orthopaedic Surgery*, Implantation Biology, CRC Press, Boca Raton, 1994, pp. 229-252.
Dutton, *Tissue Engineering: Continued Growth Expected as New Techniques Evolve*, Genetic Engineering News, Apr. 1998, pp. 21, 37.
Fernandes, et al., *Regulation of Polymeric Implants for Site-specific Drug Delivery*, Polymeric Site-specific Pharmcotherapy, Chapter 16, pp. 424-441.

Ghandehari, et al., *Genetic Engineering of Protein-Based Polymers: Potential in Controlled Drug Delivery*, Pharmaceutical Research, vol. 15, No. 6, 1998, pp. 813-815.
Harvey, *Utilizing Prostheses for Drug Delivery*, Implantation Biology, CRC Press, Boca Raton, 1994, pp. 329-345.
Heller, et al., *Controlled release of water-soluble macromolecules from Bioerodible Hydrogels*, Biomaterials 1983, vol. Oct. 4, pp. 262-266.
Kelly, *Researchers Advancing Biopolymer Systems as Vehicles for Delivering Drugs*, Genetic Engineering News, May 15, 1997, pp. 1, 25, 32, 35, 36, 41.
Langer, *1994 Whitaker Lecture: Polymers for Drug Delivery and Tissue Engineering*, Annals of Biomedical Engineering, 1995, vol. 23, pp. 101-111.
Lewis, *New Directions in Research on Blood Substitutes*, Genetic Engineering News, Jun. 15, 1997, pp. 1, 10, 12, 20, 26, 33, 35, 36, 41.
Li, et al, *A Novel Biodegradable System Based on Gelatin Nanoparticles and Poly(lactic-co-glycolic acid) Microspheres for Protein and Peptide Drug Delivery*, Journal of Pharmaceutical Sciences, vol. 86, No. 8, Aug. 1997, p. 891-895.
Masters, et al., *Liposphere Local Anesthetic Timed-Release for Perineural Site Application*, Pharmaceutical Research, vol. 15, No. 7, 1998, pp. 1038-1045.
Masters, et al., *Sustained Local Anesthetic Relapse from Bioerodible Polymer Matrices: A Potential Method for Prolonged Regional Anesthesia*, Pharmaceutical Research, vol. 10, No. 10, 1993, pp. 1527-1532.
Masters, Course Syllabus for Mayo Graduate Course, *Polymeric Site-Specific Drug Delivery*, Apr. 1998.
Masters, et al., *Prolonged Regional Nerve Blockade by Controlled Release of Local Anesthetic from a Biodegradable Polymer Matrix*, Anesthesiology, vol. 79, No. 2, 1993, pp. 340-346.
Masters, *Drug Delivery to Peripheral Nerves*, Polymeric Site-Specific Pharmacotherapy, 1994, pp. 443-455.
Morrow, *Companies to Take Broad Range of Approaches to Develop Rheumatoid Arthritis Therapies*, Genetic Engineering News, Jan. 15, 1997, pp. 1, 7, 9, 24.
Ohtani, *Three-Dimensional Organization of the Collagen Fibrillar Framework of the Human and Rat Livers*, Arch. Hist. Cytol., vol. 51, No. 5, 1988, pp. 473-788.
Peppas, et al. *New Challenges in Biomaterials*, Science, Mar. 1994, vol. 263, pp. 1715-1720.
Pramik, *Drug Delivery Firms Focus on Controlled Release Techniques*, Genetic Engineering News, Oct. 1, 1996, pp. 1, 38, 40.
Pramik, *Positive Clinical Results in Pulmonary Drug Delivery: Inhaled Insulin Effective as Injected Drug*, Genetic Engineering News, Jul. 1998, vol. 18, No. 13, pp. 1, 12, 35, 46.
Protein Polymer Technologies: 1994 Annual Report, *BioEngineered Tissue Repair and Regeneration*.
R&D, A Cahners Publication, *BioDerived Materials*, Jun. 1990, p. 58.
Ranade, *Drug Delivery Systems: 3A. Role of Polymers in Drug Delivery*, J.Clin. Pharmacol 1990; 30: 10-23.
Ranade, *Drug Delivery Systems: 3A. Role of Polymers in Drug Delivery*, J.Clin. Pharmacol 1990; 30: 107-120.
Rather, et al., *An Introduction to Materials in Medicine*, Biomaterials Science, 1996.
Sedlak, *Hyal Pharmaceutical Looks for Home Run with HIT Drug Delivery System*, Genetic Engineering News, Sep. 1, 1995, p. 16.
Sedlak, *Signal Transduction Companies Moving Some Products to the Clinical Testing Environment*, Genetic Engineering News, Mar. 15, 1997, vol. 17, No. 6, pp. 1, 27, 36.
Skarda, et al., *Biodegradable Hydrogel for Controlled Release of Biologically Active Macromolecules*, Journal of Bioactive and Compatible Polymers, vol. 8, Jan. 1993, pp. 24-40.
*Tissue Engineering*, Genetic Engineering News, Jan. 1998, pp. 33.
Urry, et al., *Protein-Based Materials with a Profound Range of Properties and Applications: The Elastin $\Delta T_t$ Hydrophobic Paradigm*, Protein-Based Materials, 1997, pp. 133-177.

\* cited by examiner

ENCAPSULATED OR COATED STENT SYSTEMS

CROSS-REFERENCE TO RELATED APPLICATIONS

This application claims the benefit under 35 U.S.C. §119 (e) of U.S. Provisional Application Ser. No. 60/478,976, filed on Jun. 17, 2003 which is hereby incorporated by reference in its entirety.

FIELD OF THE INVENTION

The present invention comprises a stent system comprising zero or more inner stents inserted into an outer stent. The inner stents and outer stent are separated and/or encapulated by a protein-based material of a protein matrix and/or a set biocoacervate, each comprising one or more biocompatible proteins and one or more biocompatible solvents. The protein-based material may also include one or more carbohydrates and one or more pharmacologically active agents.

BACKGROUND OF THE INVENTION

Stents are generally known in the medical arts. The term "stent" has been used interchangeably with terms such as "intraluminal vascular graft" and "expansible prosthesis". As used throughout this specification the term "stent" is intended to have a broad meaning and encompasses any expandable prosthetic device for implantation in a body passageway (e.g., a lumen or artery) to keep a formerly blocked passageway open and/or to provide support to weakened structures (e.g. heart walls, heart valves, venous valves and arteries).

The use of stents has attracted an increasing amount of attention due the potential of these devices to be used, in certain cases, as an alternative to surgery. Generally, a stent is used to obtain and maintain the patency of the body passageway while maintaining the integrity of the passageway. As used in this specification, the term "body passageway" is intended to have a broad meaning and encompasses any duct (e.g., natural or iatrogenic) within the human body and can include a member selected from the group comprising: blood vessels, respiratory ducts, gastrointestinal ducts and the like.

Stent development has evolved to the point where the vast majority of currently available stents rely on controlled plastic deformation of the entire structure of the stent at the target body passageway so that only sufficient force to maintain the patency of the body passageway is applied during expansion of the stent.

Generally, in many of these systems, a stent, in association with a balloon, is delivered to the target area of the body passageway by a catheter system. Once the stent has been properly located (for example, for intravascular implantation the target area of the vessel can be filled with a contrast medium to facilitate visualization during fluoroscopy), the balloon is expanded thereby plastically deforming the entire structure of the stent so that the latter is urged in place against the body passageway. As indicated above, the amount of force applied is at least that necessary to expand the stent (i.e., the applied the force exceeds the minimum force above which the stent material will undergo plastic deformation) while maintaining the patency of the body passageway. At this point, the balloon is deflated and withdrawn within the catheter, and is subsequently removed. Ideally, the stent will remain in place and maintain the target area of the body passageway substantially free of blockage (or narrowing).

See, for example, any of the following patents: U.S. Pat. No. 4,733,665 (Palmaz), U.S. Pat. No. 4,739,762 (Palmaz), U.S. Pat. No. 4,800,882 (Gianturco), U.S. Pat. No. 4,907,336 (Gianturco), U.S. Pat. No. 5,035,706 (Gianturco et al.), U.S. Pat. No. 5,037,392 (Hillstead), U.S. Pat. No. 5,041,126 (Gianturco), U.S. Pat. No. 5,102,417 (Palmaz), U.S. Pat. No. 5,147,385 (Beck et al.), U.S. Pat. No. 5,282,824 (Gianturco), U.S. Pat. No. 5,316,023 (Palmaz et al.), Canadian patent 1,239,755 (Wallsten), Canadian patent 1,245,527 (Gianturco et al.), Canadian patent application number 2,134,997 (Penn et al.), Canadian patent application number 2,171,047 (Penn et al.), Canadian patent application number 2,175,722 (Penn et al.), Canadian patent application number 2,185,740 (Penn et al.), Canadian patent application number 2,192,520 (Penn et al.), International patent application PCT/CA97/00151 (Penn et al.), International patent application PCT/CA97/00152 (Penn et al.), and International patent application PCT/CA97/00294 (Penn et al.), for a discussion on previous stent designs and deployment systems.

Furthermore, the administration of stents that carry therapeutic coatings, such as one or more polymeric coatings including pharmacologically active agents, have been utilized to reduce some of the problems created by the implantation of stents, such as restinosis and other biocompatibility responses to the foreign implant. Therefore, the search to find optimum materials and coatings, which enhance biocompatibility and prevent the occlusion of the passage through clotting or tissue growth is the ultimate goal of many manufacturers.

DETAILED DESCRIPTION OF THE INVENTION

Figure 1:
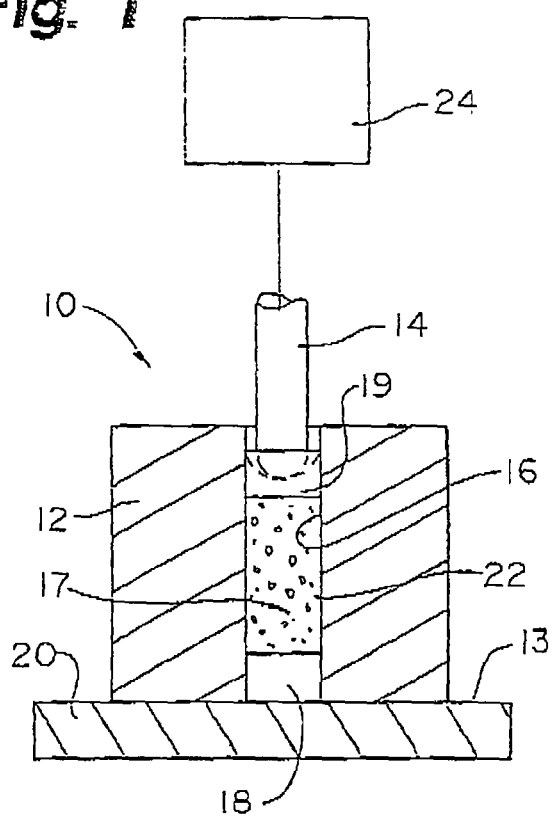
FIG. 1 is a schematic illustration, in partial cross-sectional view, of a compression molding device that may be used in the method of the present invention in a configuration prior to compression.

The embodiments of the invention described below are not intended to be exhaustive or to limit the invention to the precise forms disclosed in the following detailed description. Rather, the embodiments are chosen and described so that others skilled in the art may appreciate and understand the principles and practices of the present invention.

The present invention relates to stent systems and a method of making such systems. More specifically, the method of the present invention involves preparing one or more protein-based materials, each material comprising one or more biocompatible protein and one or more biocompatible solvents. The protein-based materials may also include one or more carbohydrates and one or more pharmacologically active agents. Once the protein-base materials are prepared, one or more stents are at least partially coated, encapsulated and/or inserted within one or more of the protein based materials. It is noted that additional polymeric materials and/or therapeutic entities may be included in the biocompatible material to provide various beneficial features such as strength, elasticity, structure and/or any other desirable characteristics. Examples of protein matrix materials and biocoacervate materials and their methods of preparation may be found in U.S. application Ser. No. 09/796,170 filed on Feb. 28, 2001, and U.S. application Ser. No. 60/497,824 filed on Aug. 26, 2003, the contents of both applications of which are incorporated by reference herein.

In one embodiment, the protein-based material may be made by providing a coatable composition that is then coated to form a film that is subsequently partially dried, formed into a cohesive body, and then compressed with the one or more stents to provide a protein matrix stent system. One embodiment of the method of preparation of a protein matrix stent system is described in the paragraphs below.

While not wishing to be bound by any theory, it is believed that by preparing a coatable composition from the aforementioned components, coating this composition to form a film that is subsequently partially dried, and then forming the film into a cohesive body, a relatively homogeneous distribution of the components is obtained in the cohesive body. Furthermore, when the film has dried enough so as to be cohesive unto itself, e.g., to a solvent content from about 50% to about 70%, subsequently formed into a cohesive body and then compressed many, if not all, of any distribution anomalies are removed or resolved. Therefore, when the protein matrix material that coats, surrounds and/or encapsulates the one or more stents includes a pharmacologically active agent, the distribution of the pharmacologically active agent is rendered substantially homogenous throughout the resulting stent system.

In addition, the removal of such distribution anomalies also includes the removal of bulk or trapped biocompatible solvent, such as aqueous solutions, i.e. bulk water (i.e., iceberg water) from the matrix. For example, in aqueous solutions, proteins bind some of the water molecules very firmly and others are either very loosely bound or form islands of water molecules between loops of folded peptide chains. Because the water molecules in such an island are thought to be oriented as in ice, which is crystalline water, the islands of water in proteins are called icebergs. Furthermore, water molecules may also form bridges between the carbonyl ($C=O$) and imino (NH) groups of adjacent peptide chains, resulting in structures similar to those of a pleated sheet ($\beta$-sheets) but with a water molecule in the position of the hydrogen bonds of that configuration. Generally, the amount of water bound to one gram of a globular protein in solution varies from 0.2 to 0.5 grams. Much larger amounts of water are mechanically immobilized between the elongated peptide chains of fibrous proteins, such as gelatin. For example, one gram of gelatin can immobilize at room temperature 25 to 30 grams of water. It is noted that other biocompatible solvents may also interact with protein molecules and the pharmacologically active agents to effect intra- and inter-molecular forces upon compression. The compression of the cohesive body removes the bulk solvent from the resulting protein matrix that surrounds or contacts the one or more stents.

The protein matrix of the present invention traps biocompatible solvent molecules, such as water molecules, and forces them to interact with the protein to produce a protein-water matrix with natural physical, biological and chemical characteristics. The compression of the cohesive body and one or more stents reduces the islands of water or bulk water resulting in a strengthened protein matrix structure. Furthermore, the reduction of bulk water enhances the homogenous characteristics of the protein matrix by reducing the pooling of water and spacing of the protein molecules and pharmacologically active agent molecules. Upon compression of the cohesive body and the one or more stents, the remaining water molecules are forced to interact with most to all protein molecules and thereby add strength, structure and stability to the protein matrix. The compression forces out most of the non-structural bulk water (immobilized water) from the matrix. As previously suggested, the bulk water is extra water that is only loosely bound to the matrix. The water that interacts with the protein molecules of the protein matrix reduces and/or prevents the protein from denaturing during compression and facilitates the protein binding with the water through intra- and inter-molecular forces (i.e., ionic, dipole-dipole such as hydrogen bonding, London dispersion, hydrophobic, etc.). The enhanced binding characteristics of the protein matrix further inhibits the loss of non-bulk solvent molecules that interact with protein molecules and/or the pharmacologically active agents. Experiments have indicated that a protein matrix dries to 25-45% water during overnight drying processes that would normally dry over 100 times that same amount of water if it were not in the matrix.

Furthermore, embodiments of the stent system of the present invention preferably have as little solvent as possible while still being cohesive and possessing the desired features relevant to the device's function, e.g., preferably a solvent content of from about 10% to about 70%, more preferably a solvent content of from about 30% to about 50%. It is found that when a stent system of the present invention includes a pharmacologically active agent, the partial drying of the film to form a cohesive body and subsequent compressing of the cohesive body, forces more solvent out of the body, thereby producing a resulting stent system that has a significantly higher concentration of pharmacologically active agent relative to other components of the system than is obtainable in stent systems produced by other methods. As a result of the substantially uniform dispersion of a greater concentration of pharmacologically active agent, a sustained, controlled release of the pharmacologically active agent is achieved, while reducing the initial high concentration effects that can be associated with other devices that include pharmacologically active agents or bolus injections of pharmacologically active agents.

Reducing the solvent content has the additional effect that the resulting stent system is more structurally sound, easy to handle, and thus, easy to insert or implant. Upon insertion, the cells of the tissue contacting the implanted protein matrix holds the stent system substantially in the desired location. Alternatively, embodiments of the stent system may be held in the desired location by tissue contact, pressure, sutures, adhesives, stent contact and/or tissue folds or creases. Embodiments of the stent system coatings may biodegrade and resorbs over time or retain their structural integrity.

To form the coatable composition, the biocompatible protein(s), the biocompatible solvent(s) and potentially the one or more carbohydrates and one or more pharmacologically active agents may be combined in any manner. It is noted that one or more additional polymeric materials and/or therapeutic entities may be added to the coatable composition during the combination step to provide additional desirable characteristics to the coatable composition. For example, the components may simply be combined in one step, or alternatively, the biocompatible protein materials may be dissolved and/or suspended in a biocompatible solvent and an additional protein material and/or the pharmacologically active agent may be dissolved and/or suspended in the same or another biocompatible solvent and then the resulting two solutions mixed.

Once prepared, the coatable composition may be coated onto any suitable surface from which it may be released after drying by any suitable method. Examples of suitable coating techniques include spin coating, gravure coating, flow coating, spray coating, coating with a brush or roller, screen printing, knife coating, curtain coating, slide curtain coating, extrusion, squeegee coating, and the like. The coated film (preferably having a substantially planar body having opposed major surfaces) is desirably thin enough so as to be capable of drying within a reasonable amount of time and also thin enough so that the film can be formed into a cohesive body comprising a substantially homogeneous dispersion of the components of the coatable composition. For example, a thinner film will tend to form a more homogeneous cohesive body when the film is formed into the shape of a cylinder. A typical coated film of the coatable composition have a thickness in the range of from about 0.01 millimeters to about 5 millimeters, more preferably from about 0.05 millimeters to about 2 millimeters.

Initially, when the film is first coated, it is likely to be non-cohesive, fluidly-flowable, and/or non self-supporting. Thus, the coated film is preferably dried sufficiently so that it becomes cohesive, i.e., the film preferably sticks to itself rather than other materials. The film may simply be allowed to dry at room temperature, or alternatively, may be dried under vacuum, conditions of mild heating, i.e., heating to a temperature of from about 25° C. to about 50° C., or conditions of mild cooling, i.e. cooling to a temperature of from about 0° C. to about 10° C. When utilizing heat to dry the film, care should be taken to avoid denaturation or structural degradation of the pharmacologically active agent incorporated therein.

The specific solvent content at which the film becomes cohesive unto itself will depend on the individual components incorporated into the coatable composition. Generally, films that have too high of a solvent content will not be cohesive. Films that have too low of a solvent content will tend to crack, shatter, or otherwise break apart upon efforts to form them into a cohesive body. With these considerations in mind, the solvent content of a partially dried film will preferably be from about 20% to about 80%, more preferably from about 30% to about 65% and most preferably from about 35% to about 50%, percentages based upon the weight of the overall composition.

Once the film is capable of forming a cohesive body, such a cohesive body may be formed by any of a number of methods. For example, the film may be rolled, folded, accordion-pleated, crumpled, or otherwise shaped such that the resulting cohesive body has a surface area that is less than that of the coated film. For example the film can be shaped into a cylinder, a cube, a sphere or the like. Preferably, the cohesive body is formed by rolling the coated film to form a cylinder.

Once so formed, the cohesive body is compressed with one or more stents to form a coated stent or stents that may be utilized in a stent system in accordance with the present invention. Any manually or automatically operable mechanical, pneumatic, hydraulic, or electrical molding device capable of subjecting the cohesive body to pressure is suitable for use in the method of the present invention. In the production of various embodiments of the present invention, a molding device may be utilized that is capable of applying a pressure of from about 20 pounds per square inch (psi) to about 100,000 psi for a time period of from about 0.5 seconds to about 48 hours. Preferably, the molding device used in the method of the present invention will be capable of applying a pressure of from about 1000 psi to about 30,000 psi for a time period of from about 2 seconds to about 60 minutes. More preferably, the molding device used in the method of the present invention will be capable of applying a pressure of from about 3,000 psi to about 25,000 psi for a time period of from about one minute to about ten minutes.

Compression molding devices suitable for use in the practice of the method of the present invention are generally known. Suitable devices may be manufactured by a number of vendors according to provided specifications, such as desirable pressure, desired materials for formulation, desired pressure source, desired size of the moldable and resulting molded device, and the like. For example, Gami Engineering, located in Mississauga, Ontario manufactures compression molding devices to specifications provided by the customer. Additionally, many compression molding devices are commercially available.

An embodiment of a compression molding device 10 suitable for use in the method of the present invention is schematically shown in FIG. 1. Compression molding device 10 is equipped with a mold body 12 in which cohesive body 22 can be subjected to pressure in order to compress and mold the cohesive body 22 into a protein matrix device in accordance with the present invention. Mold body 12 is shown supported in position on a base plate 20. More specifically, mold body 12 has provided therein a cavity 16 that preferably extends all the way through mold body 12. Within the cavity 16 a molding chamber 17 can be defined into which a cohesive body in accordance with the present invention may be inserted. The molding chamber 17 may be configured in any shape and size depending upon the shape and size of the stent system. The cavity 16 may comprise a bore of any shape that may be machined, formed, cast or otherwise provided into the mold body 12. The compression molding device may optionally include one or more apertures of approximately 0.004 to 0.0001 inches for biocompatible solvent to escape the chamber 17 during compression of the cohesive body. An inner insert 18 is preferably slidably fit within cavity 16 to be positioned against one surface 13 of the base plate 20 to define the molding chamber 17 and support to cohesive body 22 when positioned within the molding chamber 17. The insert 18 may be any shape that is desired for molding the protein matrix device. For example the insert 18 may be a solid cylindrical mandrel that can form the lumen of a tube or vessel and also hold the one or more stents. The insert 18 is thus fixed with respect to the mold body 12 to define the inner extent of the molding chamber 17. An outer insert 19 is also preferably provided to be slidable within the cavity 16.

Outer insert 19 is used to close the molding chamber 17 of cavity 16 after the inner insert 18 and the cohesive body 22 are provided in that order within the cavity 16. The inner and outer inserts 18 and 19, respectively, can be the same or different from one another, but both are preferably slidably movable within the cavity 16. The inner and outer inserts 18 and 19, respectively, are configured to create the desired form or shape of the stent system. Additionally, the inserts 18 and 19 may be shaped similarly to the shape of the cavity 16 to slide therein and are sized to effectively prevent the material of the cohesive body 22 to pass between the inserts 18 and 19 and the walls of cavity 16 when the cohesive body 22 is compressed as described below. However, the sizing may be such that moisture can escape between the outer edges of one or both inserts 18 and 19 and the surface walls of the cavity 16 from the cohesive body 22 during compression. Otherwise, other conventional or developed means can be provided to permit moisture to escape from the mold cavity during compression. For example, small openings could pass through one or both of the inserts 18 and 19 or mold body 12 which may also include one-way valve devices. Insert 18 may be eliminated so that surface 13 of base plate 20 defines the lower constraint to molding chamber 17. However, the use of insert 18 is beneficial, in that its presence facilitates easy removal of the cohesive body 22 after compression (described below) and provides a sufficiently hard surface against which the cohesive body 22 can be compressed. Moreover, by utilizing a series of differently sized and/or shaped inner inserts 18, the volume of the molding chamber can be varied, or different end features may be provided to the cohesive body 22. Outer inserts 19 can likewise be varied.

Outer insert 19 is also positioned to be advanced within cavity 16 or retracted from cavity 16 by a plunger 14. Preferably, the contacting surfaces of outer insert 19 and plunger 14 provide a cooperating alignment structure so that pressure can be evenly applied to the cohesive body 22. The plunger 14 may comprise a part of, or may be operatively connected with a pressure generation mechanism 24 that has the ability to apply pressure of the type and force necessary to achieve the results of the present invention. Conventional or developed technologies are contemplated, such as using mechanical, hydraulic, pneumatic, electrical, or other systems. Such systems can be manually or automatically operable.

Plunger 14 operates independently of mold body 12 and is operationally coupled to the pressure generation mechanism 24. Pressure generation mechanism 24 may be any pressure source capable of applying from about 20 psi to about 100,000 psi for a time period of from about 0.5 seconds to about 48 hours, preferably capable of applying from about 1000 psi to about 30,000 psi for a time period of from about 10 seconds to about 60 minutes, and more preferably, capable of applying a pressure of from about 3000 psi to about 25,000 psi for a time period of from about 1 minute to about 10 minutes. Preferably, plunger 14 is formulated of a material capable of translating substantially all of the pressure applied by pressure generation mechanism 24 to cohesive body 22.

Mold body 12 may be fabricated from any material capable of withstanding the pressure to be applied from pressure generation mechanism 24, e.g., high density polyethylene, Teflon®, steel, stainless steel, aluminum, titanium, brass, copper, combinations of these and the like. Desirably, mold body 12 is fabricated from a material that provides low surface friction to inserts 18 and 19 and cohesive body 22. Alternatively, surfaces defining the cavity 16 may be coated with a low friction material, e.g., Teflon®, to provide such low surface friction. Due to its relatively low cost, sufficient strength and surface friction characteristics, mold body 12 is desirably fabricated from steel or brass. Cavity 16, extending substantially through mold body 12, may be of any shape and configuration, as determined by the desired configuration of the resulting, compressed stent systems. In one embodiment, cavity 16 is cylindrical. However, the shape of the cavity 16 can be configured to accommodate the shape and size of the resulting, compressed stent system. As above, inserts 18 and 19 preferably fit within cavity 16 in a manner that allows moisture to escape from mold body 12, and so that inserts 18 and 19 may be easily inserted into and removed from cavity 16. Furthermore, it is preferred that inserts 18 and 19 fit within cavity 16 in a manner that provides adequate support and containment for cohesive body 22, so that, upon compression, the material of cohesive body 22 does not escape cavity 16 in a manner that would produce irregularly shaped edges on the resulting stent system.

Figure 2:
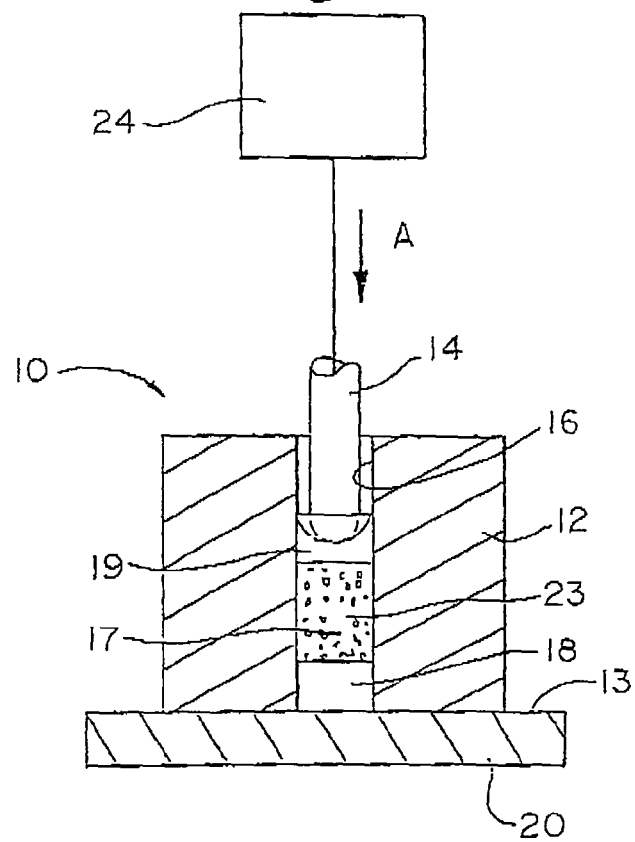
FIG. 2 is a schematic illustration, in partial cross-sectional view, of a compression molding device that may be used in the method of the present invention in a configuration during compression.

According to one procedure for using compression molding device 10 to carry out the method of the present invention, the mold body 12 is positioned as shown in FIG. 1 on the base plate 20, which itself may be supported in any manner. Then, an inner insert 18 is placed into cavity 16 followed by a cohesive body 22 and one or more stents to be compressed and an outer insert 19 as shown. Plunger 14 is then positioned so as to be in driving engagement with outer insert 19. Then, as schematically illustrated in FIG. 2, the pressure generation mechanism 24 is activated to move plunger 14 in the direction of arrow A to reduce the volume of the molding cavity 17 to make a compressed cohesive body 23. Pressure generation mechanism 24 applies sufficient pressure, i.e., from about 20 psi to about 100,000 psi for a time period of from about 0.5 seconds to about 48 hours, to plunger 14, insert 19 and cohesive body 22 against the inner insert 18, thereby driving moisture from and compressing cohesive body 22 into a stent system in accordance with the present invention.

Figure 3:
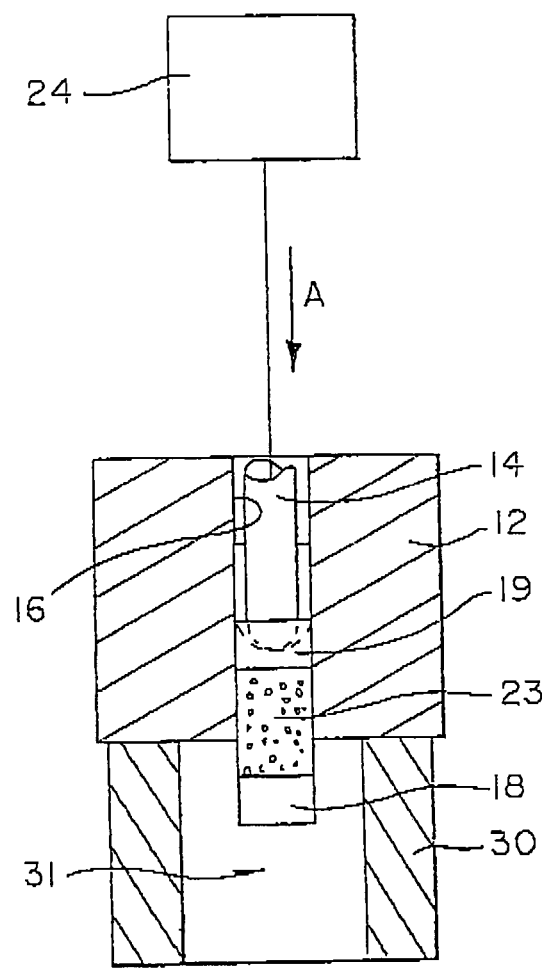
FIG. 3 is a schematic illustration, in partial cross-sectional view, of a compression molding device that may be used in the method of the present invention in a configuration during ejection.

As shown in FIG. 3, the compressed cohesive body 23 and stents can then be ejected from the mold body 12 along with inserts 18 and 19 by positioning the mold body 12 on a support spacer 30 and further advancing the plunger 14 in the direction of arrow A by the pressure generation mechanism 24. Generally, base plate 20 is separated from the mold body 12 when ejecting the stent system and inserts 18 and 19. The support spacer 30 is preferably shaped and dimensioned to provide an open volume 31 for the compressed cohesive body 23 to be easily removed. That is, when the plunger 14 is sufficiently advanced, the insert 18 and compressed cohesive body 23 can fall into the open volume 31 within the support spacer 30. After completion, the plunger 14 can be fully retracted so that the compression molding device 10 can be reconfigured for a next operation.

Any biocompatible protein material may be utilized in the stent systems and corresponding methods of the present invention. Preferably, any such material will at least be water-compatible, and more preferably will be water-absorbing or hydrogel forming. Furthermore, one or more biocompatible protein materials may be incorporated into the protein matrix device of the present invention and may desirably be selected based upon their biocompatible and/or degradation properties. The combination of more than one biocompatible protein can be utilized to mimic the environment in which the system is to be administered, optimize the biofunctional characteristics, such as cell attachment and growth, nonimmuno-response reaction and/or alter the release characteristics, or duration of an included pharmacologically active agent, if a pharmacologically active agent is to be included in the device.

Additionally, the proteins of the present invention are generally purified and in a free-form state. Normally, free-form proteins are comprised of protein molecules that are not substantially crosslinked to other protein molecules, unlike tissues or gelatins. Normally, tissue or gelatin is already in a crosslinked matrix form and is thereby limited in forming new intermolecular or intramolecular bonds. Therefore, the free-form protein molecules when added to solvent have the capacity to freely associate or intermingle with each other and other molecules or particles, such as solvents or pharmacologically active agents to form a homogeneous structure. Additionally, the binding sites of the free-form primary proteins for the attraction and retention of proteoglycans or secondary proteins are generally available for binding whereas proteins derived from tissues and gelatins have generally lost some or most of its binding capability.

Also the proteins of the present invention are generally purified proteins. The purity of each protein component mixed in the coatable film or the solution phase (the process of making the coacervates and biomaterials will be described further below) during production of the compressed protein matrix or the coacervate include 20% or less other proteins or impurities, preferably 10% or less other proteins or impurities, more preferably 3% or less other proteins or impurities and if available ideally 1% or less other proteins or impurities.

The biocompatible protein material comprises one or more biocompatible synthetic protein, genetically-engineered protein, natural protein or any combination thereof. In many embodiments of the present invention, the biocompatible protein material comprises a water-absorbing, biocompatible protein. In various embodiments of the present invention, the utilization of a water-absorbing biocompatible protein provides the advantage that, not only will the protein matrix device be biodegradable, but also resorbable. That is, that the metabolites of the degradation of the water-absorbing biodegradable protein may be reused by the patient's body rather than excreted. In other embodiments that do not degrade or resorb the water absorbing material provides enhanced biocompatible characteristics since the stent system is generally administered to environments that contain water.

The biocompatible protein utilized may either be naturally occurring, synthetic or genetically engineered. Naturally occurring protein that may be utilized in the protein matrix device of the present invention include, but are not limited to elastin, collagen, albumin, keratin, fibronectin, silk, silk fibroin, actin, myosin, fibrinogen, thrombin, aprotinin, antithrombin III and any other biocompatible natural protein. It is noted that combinations of natural proteins may be utilized to optimize desirable characteristics of the resulting protein matrix, such as strength, degradability, resorption, etc. Inasmuch as heterogeneity in molecular weight, sequence and stereochemistry can influence the function of a protein in a stent system, in some embodiments of the present invention synthetic or genetically engineered proteins are preferred in that a higher degree of control can be exercised over these parameters.

Examples of natural free-form proteins that are commercially available and may be utilized in some embodiments of the present invention include Type I soluble or insoluble collagen, insoluble or soluble elastin, and soluble albumen manufactured by Kensey Nash Corporation, 55 East Uwchlan Avenue, Exton, Pa. 19341, Sigma-Aldrich Corporation, St. Louis, Mo., USA or Elastin Products Company, Inc., P.O. Box 568, Owensville, Mo., USA 65066. It is noted that combinations of natural proteins may be utilized to optimize desirable characteristics of the resulting protein-based materials, such as strength, degradability, resorption, etc. Inasmuch as heterogeneity in molecular weight, sequence and stereochemistry can influence the function of a protein in a protein-based material, in some embodiments of the present invention synthetic or genetically engineered proteins are preferred in that a higher degree of control can be exercised over these parameters.

Synthetic proteins are generally prepared by chemical synthesis utilizing techniques known in the art. Examples of such synthetic proteins include but are not limited to natural protein made synthetically and collagen linked glycosaminoglycans (GAGs) like collagen-heparin, collagen-chondroitin and the like. Also, individual proteins may be chemically combined with one or more other proteins of the same or different type to produce a dimer, trimer or other multimer. A simple advantage of having a larger protein molecule is that it will make interconnections with other protein molecules to create a stronger protein-based material that is less susceptible to dissolving in aqueous solutions.

Additional, protein molecules can also be chemically combined to any other chemical so that the chemical does not release from the matrix. In this way, the chemical entity can provide surface modifications to the matrix or structural contributions to the matrix to produce specific characteristics. The surface modifications can enhance and/or facilitate cell attachment depending on the chemical substance or the cell type. The structural modifications can be used to facilitate or impede dissolution, enzymatic degradation or dissolution of the matrix.

Synthetic biocompatible materials may be cross-linked, linked, bonded or chemically and/or physically linked to pharmacological active agents and utilized alone or in combination with other biocompatible proteins to form the cohesive body. Examples of such cohesive body materials include, but are not limited to heparin-protein, heparin-polymer, chondroitin-protein, chondroitin-polymer, heparin-cellulose, heparin-alginate, heparin-polylactide, GAGs-collagen, heparin-collagen-condroitin and heparin-collagen.

Other proteins that may be utilized in various embodiments of the present invention include genetically engineered proteins. Specific examples of a particularly preferred genetically engineered proteins for use in the stent systems of the present invention is that commercially available under the nomenclature "ELP", "SLP", "CLP", "SLPL", "SLPF" and "SELP" from Protein Polymer Technologies, Inc. San Diego, Calif. ELP's, SLP's, CLP's, SLPL's, SLPF's and SELP's are families of genetically engineered protein polymers consisting of silklike blocks, elastinlike blocks, collagenlike blocks, lamininlike blocks, fibronectinlike blocks and the combination of silklike and elastinlike blocks, respectively. The ELP's, SLP's, CLP's, SLPL's, SLPF's and SELP's are produced in various block lengths and compositional ratios. Generally, blocks include groups of repeating amino acids making up a peptide sequence that occurs in a protein. Genetically engineered proteins are qualitatively distinguished from sequential polypeptides found in nature in that the length of their block repeats can be greater (up to several hundred amino acids versus less than ten for sequential polypeptides) and the sequence of their block repeats can be almost infinitely complex. Table A depicts examples of genetically engineered blocks. Table A and a further description of genetically engineered blocks may be found in Franco A. Ferrari and Joseph Cappello, *Biosynthesis of Protein Polymers*, in: Protein-Based Materials, (eds., Kevin McGrath and David Kaplan), Chapter 2, pp. 37-60, Birkhauser, Boston (1997).

TABLE A

Protein polymer sequences

| Polymer Name | Monomer Amino Acid Sequence |
|---|---|
| SLP 3 | $[(GAGAGS)_9 GAAGY)]$ |
| SLP 4 | $(GAGAGS)_n$ |
| SLP F | $[(GAGAGS)_9 GAA\ VTGRGDSPAS\ AAGY]_n$ |
| SLP L3.0 | $[(GAGAGS)_9 GAA\ PGASIKVAVSAGPS\ AGY]_n$ |
| SLP L3.1 | $[(GAGAGS)_9 GAA\ PGASIKVAVSGPS\ AGY]_n$ |
| SLP F9 | $[(GAGAGS)_9 RYVVLPRPVCFEK\ AAGY]_n$ |
| ELP I | $[(VPGVG)_4]_n$ |
| SELP 0 | $[(GVGVP)_8 (GAGAGS)_2]_n$ |
| SELP 1 | $[GAA\ (VPGVG)_4\ VAAGY\ (GAGAGS)_9]_n$ |
| SELP 2 | $[(GAGAGS)_6 GAAGY\ (GAGAGS)_5 (GVGVP)_8]_n$ |
| SELP 3 | $[(GVGVP)_8 (GAGAGS)_8]_n$ |
| SELP 4 | $[(GVGVP)_{12} (GAGAGS)_8]_n$ |
| SELP 5 | $[(GVGVP)_{16} (GAGAGS)_8]_n$ |
| SELP 6 | $[(GVGVP)_{32} (GAGAGS)_8]_n$ |
| SELP 7 | $[(GVGVP)_8 (GAGAGS)_6]_n$ |
| SELP 8 | $[(GVGVP)_8 (GAGAGS)_4]_n$ |
| KLP 1.2 | $[(AKLKLAEAKLELAE)_4]_n$ |
| CLP 1 | $[GAP(GPP)_4]_n$ |
| CLP 2 | $\{[GAP(GPP)_4]_2\ GPAGPVGSP\}_n$ |
| CLP-CB | $\{[GAP(GPP)_4]_2$ (GLPGPKGDRGDAGPKGADGSPGPA) $GPAGPVGSP\}_n$ |
| CLP 3 | $(GAPGAPGSQGAPGLQ)_n$ |

Repetitive amino acid sequences of selected protein polymers.
SLP = silk like protein;
SLPF = SLP containing the RGD sequence from fibronectin;
SLPL 3/0 and SLPL 3/1 = SLP containing two difference sequences from laminin protein;
ELP = elastin like protein;
SELP = silk elastin like protein;
CLP = collagen like protein;
CLP-CB = CLP containing a cell binding domain from human collagen;
KLP = keratin like protein.

The nature of the elastinlike blocks, and their length and position within the monomers influences the water solubility of the SELP polymers. For example, decreasing the length and/or content of the silklike block domains, while maintaining the length of the elastinlike block domains, increases the water solubility of the polymers. For a more detailed discussion of the production of SLP's, ELP's, CLP's, SLPF's and SELP's as well as their properties and characteristics see, for example, in J. Cappello et al., *Biotechnol. Prog.*, 6, 198 (1990), the full disclosure of which is incorporated by reference herein. One preferred SELP, SELP7, has an elastin:silk ratio of 1.33, and has 45% silklike protein material and is believed to have weight average molecular weight of 80,338.

The amount of the biocompatible protein component utilized in the coatable composition will be dependent upon the amount of coatable composition desired in relation to the other components of the stent system and the particular biocompatible protein component chosen for use in the coatable composition. Furthermore, the amount of coatable composition utilized in the coating of the film will be determinative of the size of the film, and thus, the size of the cohesive body and the resulting stent system. That is, inasmuch as the amounts of the remaining components are dependent upon the amount of biocompatible protein component utilized, the amount of biocompatible protein component may be chosen based upon the aforementioned parameters.

Any biocompatible solvent may be utilized in the method and corresponding stent system of the present invention. By using a biocompatible solvent, the risk of adverse tissue reactions to residual solvent remaining in the device after manufacture is minimized. Additionally, the use of a biocompatible solvent reduces the potential structural and/or pharmacological degradation of the pharmacologically active agent that some such pharmacologically active agents undergo when exposed to organic solvents. Suitable biocompatible solvents for use in the method of the present invention include, but are not limited to, water; dimethyl sulfoxide (DMSO); biocompatible alcohols, such as methanol and ethanol; polyols such as glycerol, various acids, such as formic acid; oils, such as olive oil, peanut oil and the like; ethylene glycol, glycols; and combinations of these and the like. Preferably, the biocompatible solvent comprises water. The amount of biocompatible solvent utilized in the coatable composition will preferably be that amount sufficient to result in the composition being fluid and flowable enough to be coatable. Generally, the amount of biocompatible solvent suitable for use in the method of the present invention to prepare the coatable composition will range from about 50% to about 500%, preferably from about 100% to about 300% by weight, based upon the weight of the biodegradable polymeric material.

In addition to the biocompatible protein(s) and the biocompatible solvent(s), the coacervates or biomaterial that may be utilized in various embodiments of the present invention may include one or more pharmacologically active agents. Generally, the distribution of the pharmacologically active agent is rendered substantially homogenous throughout the resulting protein matrix, coacervate or biomaterial. As used herein, "pharmacologically active agent" generally refers to a pharmacologically active agent having a direct or indirect beneficial therapeutic effect upon introduction into a host. Pharmacologically active agents further includes neutraceuticals. The phrase "pharmacologically active agent" is also meant to indicate prodrug forms thereof. A "prodrug form" of a pharmacologically active agent means a structurally related compound or derivative of the pharmacologically active agent which, when administered to a host is converted into the desired pharmacologically active agent. A prodrug form may have little or none of the desired pharmacological activity exhibited by the pharmacologically active agent to which it is converted. Representative examples of pharmacologically active agents that may be suitable for use in the protein matrix materials, coacervates, or resulting biomaterials utilized in embodiments of the present invention include, but are not limited to, (grouped by therapeutic class):

Antidiarrhoeals such as diphenoxylate, loperamide and hyoscyamine;
Antihypertensives such as hydralazine, minoxidil, captopril, enalapril, clonidine, prazosin, debrisoquine, diazoxide, guanethidine, methyldopa, reserpine, trimethaphan;
Calcium channel blockers such as diltiazem, felodipine, amlodipine, nitrendipine, nifedipine and verapamil;
Antiarrhyrthmics such as amiodarone, flecainide, disopyramide, procainamide, mexiletene and quinidine,
Antiangina agents such as glyceryl trinitrate, erythrityl tetranitrate, pentaerythritol tetranitrate, mannitol hexanitrate, perhexilene, isosorbide dinitrate and nicorandil;

Beta-adrenergic blocking agents such as alprenolol, atenolol, bupranolol, carteolol, labetalol, metoprolol, nadolol, nadoxolol, oxprenolol, pindolol, propranolol, sotalol, timolol and timolol maleate;

Cardiotonic glycosides such as digoxin and other cardiac glycosides and theophylline derivatives;

Adrenergic stimulants such as adrenaline, ephedrine, fenoterol, isoprenaline, orciprenaline, rimeterol, salbutamol, salmeterol, terbutaline, dobutamine, phenylephrine, phenylpropanolamine, pseudoephedrine and dopamine;

Vasodilators such as cyclandelate, isoxsuprine, papaverine, dipyrimadole, isosorbide dinitrate, phentolamine, nicotinyl alcohol, co-dergocrine, nicotinic acid, glycerl trinitrate, pentaerythritol tetranitrate and xanthinol;

Antiproliferative agents such as paclitaxel, actinomycin D, sirolimus, tacrolimus, everolimus and dexamethasone;

Antimigraine preparations such as ergotanmine, dihydro-ergotamine, methysergide, pizotifen and sumatriptan;

Anticoagulants and thrombolytic agents such as warfarin, dicoumarol, heparin including low molecular weight heparins such as enoxaparin, streptokinase and its active derivatives, chondroitin sulfate, hirudin;

Hemostatic agents such as aprotinin, tranexamic acid and protamine;

Analgesics and antipyretics including the opioid analgesics such as buprenorphine, dextromoramide, dextropropoxyphene, fentanyl, alfentanil, sufentanil, hydromorphone, methadone, morphine, oxycodone, papaveretum, pentazocine, pethidine, phenopefidine, codeine dihydrocodeine; acetylsalicylic acid (aspirin), paracetamol, and phenazone;

Immunosuppressants, antiproliferatives and cytostatic agents such as rapomycin (sirolimus) and its analogs (everolimus and tacrolimus);

Neurotoxins such as capsaicin, botulinum toxin (botox);

Hypnotics and sedatives such as the barbiturates amylobarbitone, butobarbitone and pentobarbitone and other hypnotics and sedatives such as chloral hydrate, chlormethiazole, hydroxyzine and meprobamate;

Antianxiety agents such as the benzodiazepines alprazolam, bromazepam, chlordiazepoxide, clobazam, chlorazepate, diazepam, flunitrazepam, flurazepam, lorazepam, nitrazepam, oxazepam, temazepam and triazolam;

Neuroleptic and antipsychotic drugs such as the phenothiazines, chlorpromazine, fluphenazine, pericyazine, perphenazine, promazine, thiopropazate, thioridazine, trifluoperazine; and butyrophenone, droperidol and haloperidol; and other antipsychotic drugs such as pimozide, thiothixene and lithium;

Antidepressants such as the tricyclic antidepressants amitryptyline, clomipramine, desipramine, dothiepin, doxepin, imipramine, nortriptyline, opipramol, protriptyline and trimipramine and the tetracyclic antidepressants such as mianserin and the monoamine oxidase inhibitors such as isocarboxazid, phenelizine, tranylcypromine and moclobemide and selective serotonin re-uptake inhibitors such as fluoxetine, paroxetine, citalopram, fluvoxamine and sertraline;

CNS stimulants such as caffeine and 3-(2-aminobutyl) indole;

Anti-alzheimer's agents such as tacrine;

Anti-Parkinson's agents such as amantadine, benserazide, carbidopa, levodopa, benztropine, biperiden, benzhexol, procyclidine and dopamine-2 agonists such as S(−)-2-(N-propyl-N-2-thienylethylamino)-5-hydroxytetralin (N-0923), Anticonvulsants such as phenytoin, valproic acid, primidone, phenobarbitone, methylphenobarbitone and carbamazepine, ethosuximide, methsuximide, phensuximide, sulthiame and clonazepam, Antiemetics and antinauseants such as the phenothiazines prochloperazine, thiethylperazine and 5HT-3 receptor antagonists such as ondansetron and granisetron, as well as dimenhydrinate, diphenhydramine, metoclopramide, domperidone, hyoscine, hyoscine hydrobromide, hyoscine hydrochloride, clebopride and brompride;

Non-steroidal anti-inflammatory agents including their racemic mixtures or individual enantiomers where applicable, preferably which can be formulated in combination with dermal and/or mucosal penetration enhancers, such as ibuprofen, flurbiprofen, ketoprofen, aclofenac, diclofenac, aloxiprin, aproxen, aspirin, diflunisal, fenoprofen, indomethacin, mefenamic acid, naproxen, phenylbutazone, piroxicam, salicylamide, salicylic acid, sulindac, desoxysulindac, tenoxicam, tramadol, ketorolac, flufenisal, salsalate, triethanolamine salicylate, aminopyrine, antipyrine, oxyphenbutazone, apazone, cintazone, flufenamic acid, clonixerl, clonixin, meclofenamic acid, flunixin, coichicine, demecolcine, allopurinol, oxypurinol, benzydamine hydrochloride, dimefadane, indoxole, intrazole, mimbane hydrochloride, paranylene hydrochloride, tetrydamine, benzindopyrine hydrochloride, fluprofen, ibufenac, naproxol, fenbufen, cinchophen, diflumidone sodium, fenamole, flutiazin, metazamide, letimide hydrochloride, nexeridine hydrochloride, octazamide, molinazole, neocinchophen, nimazole, proxazole citrate, tesicam, tesimide, tolmetin, and triflumidate;

Antirheumatoid agents such as penicillamine, aurothioglucose, sodium aurothiomalate, methotrexate and auranofin;

Muscle relaxants such as baclofen, diazepam, cyclobenzaprine hydrochloride, dantrolene, methocarbamol, orphenadrine and quinine;

Agents used in gout and hyperuricaemia such as allopurinol, colchicine, probenecid and sulphinpyrazone;

Oestrogens such as oestradiol, oestriol, oestrone, ethinyloestradiol, mestranol, stilboestrol, dienoestrol, epioestriol, estropipate and zeranol;

Progesterone and other progestagens such as allyloestrenol, dydrgesterone, lynoestrenol, norgestrel, norethyndrel, norethisterone, norethisterone acetate, gestodene, levonorgestrel, medroxyprogesterone and megestrol;

Antiandrogens such as cyproterone acetate and danazol;

Antioestrogens such as tamoxifen and epitiostanol and the aromatase inhibitors, exemestane and 4-hydroxy-androstenedione and its derivatives;

Androgens and anabolic agents such as testosterone, methyltestosterone, clostebol acetate, drostanolone, furazabol, nandrolone oxandrolone, stanozolol, trenbolone acetate, dihydro-testosterone, 17-(α-methyl-19-noriestosterone and fluoxymesterone;

5-alpha reductase inhibitors such as finasteride, turosteride, LY-191704 and MK-306;

Corticosteroids such as betamethasone, betamethasone valerate, cortisone, dexamethasone, dexamethasone 21-phosphate, fludrocortisone, flumethasone, fluocinonide, fluocinonide desonide, fluocinolone, fluocinolone acetonide, fluocortolone, halcinonide, halopredone, hydrocortisone, hydrocortisone 17-valerate, hydrocortisone 17-butyrate, hydrocortisone 21-acetate, methylprednisolone, prednisolone, prednisolone 21-phosphate, prednisone, triamcinolone, triamcinolone acetonide;

Glycosylated proteins, proteoglycans, glycosaminoglycans such as chondroitin sulfate; heparan sulfate, chitin, acetyl-glucosamine, hyaluronic acid;

Complex carbohydrates such as glucans;

Further examples of steroidal anti-inflammatory agents such as cortodoxone, fludroracetonide, fludrocortisone, difluorsone diacetate, flurandrenolone acetonide, medrysone, amcinafel, amcinafide, betamethasone and its other esters, chloroprednisone, clorcortelone, descinolone, desonide, dichlorisone, difluprednate, flucloronide, flumethasone, flunisolide, flucortolone, fluorometholone, fluperolone, fluprednisolone, meprednisone, methylmeprednisolone, paramethasone, cortisone acetate, hydrocortisone cyclopentylpropionate, cortodoxone, flucetonide, fludrocortisone acetate, flurandrenolone, aincinafal, amcinafide, betamethasone, betamethasone benzoate, chloroprednisone acetate, clocortolone acetate, descinolone acetonide, desoximetasone, dichlorisone acetate, difluprednate, flucloronide, flumethasone pivalate, flunisolide acetate, fluperolone acetate, fluprednisolone valerate, paramethasone acetate, prednisolamate, prednival, triamcinolone hexacetonide, cortivazol, formocortal and nivazol;

Pituitary hormones and their active derivatives or analogs such as corticotrophin, thyrotropin, follicle stimulating hormone (FSH), luteinising hormone (LH) and gonadotrophin releasing hormone (GnRH);

Hypoglycemic agents such as insulin, chlorpropamide, glibenclamide, gliclazide, glipizide, tolazamide, tolbutamide and metformin;

Thyroid hormones such as calcitonin, thyroxine and liothyronine and antithyroid agents such as carbimazole and propylthiouracil;

Other miscellaneous hormone agents such as octreotide;

Pituitary inhibitors such as bromocriptine;

Ovulation inducers such as clomiphene;

Diuretics such as the thiazides, related diuretics and loop diuretics, bendrofluazide, chlorothiazide, chlorthalidone, dopamine, cyclopenthiazide, hydrochlorothiazide, indapamide, mefruside, methycholthiazide, metolazone, quinethazone, bumetanide, ethacrynic acid and frusemide and potassium sparing diuretics, spironolactone, amiloride and triamterene;

Antidiuretics such as desmopressin, lypressin and vasopressin including their active derivatives or analogs;

Obstetric drugs including agents acting on the uterus such as ergometrine, oxytocin and gemeprost;

Prostaglandins such as alprostadil (PGE1), prostacyclin (PGI2), dinoprost (prostaglandin F2-alpha) and misoprostol;

Antimicrobials including the cephalosporins such as cephalexin, cefoxytin and cephalothin;

Penicillins such as amoxycillin, amoxycillin with clavulanic acid, ampicillin, bacampicillin, benzathine penicillin, benzylpenicillin, carbenicillin, cloxacillin, methicillin, phenethicillin, phenoxymethylpenicillin, flucloxacillin, meziocillin, piperacillin, ticarcillin and azlocillin;

Tetracyclines such as minocycline, chlortetracycline, tetracycline, demeclocycline, doxycycline, methacycline and oxytetracycline and other tetracycline-type antibiotics;

Amnioglycoides such as amikacin, gentamicin, kanamycin, neomycin, netilmicin and tobramycin;

Anti fungals such as amorolfine, isoconazole, clotrimazole, econazole, miconazole, nystatin, terbinafine, bifonazole, amphotericin, griseofulvin, ketoconazole, fluconazole and flucytosine, salicylic acid, fezatione, ticlatone, tolnaftate, triacetin, zinc, pyrithione and sodium pyrithione;

Quinolones such as nalidixic acid, cinoxacin, ciprofloxacin, enoxacin and norfloxacin;

Sulphonamides such as phthalysulphthiazole, sulfadoxine, sulphadiazine, sulphamethizole and sulphamethoxazole;

Sulphones such as dapsone;

Other miscellaneous antibiotics such as chloramphenicol, clindamycin, erythromycin, erythromycin ethyl carbonate, erythromycin estolate, erythromycin glucepate, erythromycin ethylsuccinate, erythromycin lactobionate, roxithromycin, lincomycin, natamycin, nitrofurantoin, spectinomycin, vancomycin, aztreonarn, colistin IV, metronidazole, tinidazole, fusidic acid, trimethoprim, and 2-thiopyridine N-oxide; halogen compounds, particularly iodine and iodine compounds such as iodine-PVP complex and diiodohydroxyquin, hexachlorophene; chlorhexidine; chloroamine compounds; and benzoylperoxide;

Antituberculosis drugs such as ethambutol, isoniazid, pyrazinamide, rifampicin and clofazimine;

Antimalarials such as primaquine, pyrimethamine, chloroquine, hydroxychloroquine, quinine, mefloquine and halofantrine;

Antiviral agents such as acyclovir and acyclovir prodrugs, famcyclovir, zidovudine, didanosine, stavudine, lamivudine, zalcitabine, saquinavir, indinavir, ritonavir, n-docosanol, tromantadine and idoxuridine;

Anthelmintics such as mebendazole, thiabendazole, niclosamide, praziquantel, pyrantel embonate and diethylcarbamazine;

Cytotoxic agents such as plicamycin, cyclophosphamide, dacarbazine, fluorouracil and its prodrugs (described, for example, in *International Journal of Pharmaceutics*, 111, 223-233 (1994)), methotrexate, procarbazine, 6-mercaptopurine and mucophenolic acid;

Anorectic and weight reducing agents including dexfenfluramine, fenfluramine, diethylpropion, mazindol and phentermine;

Agents used in hypercalcaemia such as calcitriol, dihydrotachysterol and their active derivatives or analogs;

Antitussives such as ethylmorphine, dextromethorphan and pholcodine;

Expectorants such as carbolcysteine, bromhexine, emetine, quanifesin, ipecacuanha and saponins;

Decongestants such as phenylephrine, phenylpropanolamine and pseudo ephedrine;

Bronchospasm relaxants such as ephedrine, fenoterol, orciprenaline, rimiterol, salbutamol, sodium cromoglycate, cromoglycic acid and its prodrugs (described, for example, in *International Journal ofpharmaceutics* 7, 63-75 (1980)), terbutaline, ipratropium bromide, salmeterol and theophylline and theophylline derivatives;

Antihistamines such as meclozine, cyclizine, chlorcyclizine, hydroxyzine, brompheniramine, chlorpheniramine, clemastine, cyproheptadine, dexchlorpheniramine, diphenhydramine, diphenylamine, doxylamine, mebhydrolin, pheniramine, tripolidine, azatadine, diphenylpyraline, methdilazine, terfenadine, astemizole, loratidine and cetirizine;

Local anaesthetics such as benzocaine, bupivacaine, amethocaine, lignocaine, lidocaine, cocaine, cinchocaine, dibucaine, mepivacaine, prilocaine, etidocaine, veratridine (specific c-fiber blocker) and procaine;

Stratum corneum lipids, such as ceramides, cholesterol and free fatty acids, for improved skin barrier repair [Man, et al. *J. Invest. Dermatol.,* 106(5), 1096, (1996)];

Neuromuscular blocking agents such as suxamethonium, alcuronium, pancuronium, atracurium, curarie, gallamine, tubocurarine and vecuronium;

Smoking cessation agents such as nicotine, bupropion and ibogaine;

Insecticides and other pesticides which are suitable for local application;

Dermatological agents, such as vitamins A, C, B1, B2, B6, B12, B12α., and E, vitamin E acetate and vitamin E sorbate;

Allergens for desensitisation such as house, dust or mite allergens;

Nutritional agents and neutraceuticals, such as vitamins, essential amino acids and fats;

Macromolecular pharmacologically active agents such as proteins, enzymes, peptides, polysaccharides (such as cellulose, amylose, dextran, chitin), nucleic acids, cells, tissues, and the like;

Wound healing agents and growth factors that help cells to more closely mend wounds to regenerate host tissue to its original form, such as polypeptide growth factors (e.g. EGF, FGF, PDGF, TGF, VEGF, NGF, HGH)

Bone mending biochemicals such as calcium carbonate, calcium phosphate, hydroxyapetite or bone morphogenic protein (BMP);

Angiogenic growth factors such as Vascular Endothelial Growth Factor (VEGF) and epidermal growth factor (EFG), cytokines interleukins, fibroblasts and cytotaxic chemicals; and Keratolytics such as the alpha-hydroxy acids, glycolic acid and salicylic acid; and DNA, RNA or other oligonucleotides.

The stent systems as disclosed herein may also be utilized for DNA delivery, either naked DNA, plasma DNA or any size DNA delivery. Also, the protein matrix may be utilized for delivery of RNA types of senses, or oligonucleotides that may be man-made portions of DNA or RNA. The protein matrix could also be utilized for delivery of compounds, as explained anywhere herein, in ovum or in embryos, as the site for implantation of the protein matrix.

The DNA, RNA or oligonucleotide may be incorporated into the protein matrix utilizing the same process of making the stent system as described above. The only difference would be that the pharmacological active agents utilized would be the DNA, RNA, oligonucleotides and other such materials. In one example, a cohesive body may be produced by making a composition containing one or more biocompatible proteins, one or more biocompatible solvents, one or more stents and an antisense type material. In general the complementary strand of a coding sequence of DNA is the cDNA and the complementary strand of MRNA is the antisense RNA. In various embodiments of the present invention, antisense material delivered by a stent system of the present invention binds with mRNA, thereby preventing it from making the protein.

Two of the advantages of including DNA, RNA or oligonucleotides in a stent system is that such a system includes the benefits of local drug delivery to target cells and to have a controlled time release component so that there is an extended delivery period. An additional advantage to delivery of DNA, RNA or oligonucleotides components is that the DNA, RNA or oligonucleotides components can be released in a systematic and controlled manner over a long period of time. For example, when the antisense components bind with RNA, the body tends to cleave the RNA thereby inhibiting protein production. The biological system responds by making more RNA to make proteins. The stent system provides delivery of additional antisense components in a location for an extended period of time, thereby blocking the production of the undesired protein. Also the biocompatibility of the protein matrix material enhances the binding characteristics of the anitsense components to their proper binding sites. Since the protein matrix material can be fabricated or produced to resemble the host tissue, the host cells are able to better interact with the administered protein matrix device, thereby facilitating the binding of the complimentary antisense components delivered by the protein matrix with the DNA and RNA in the host cells.

The protein matrix and/or biocoacervate material used in embodiments of the present invention is particularly advantageous for the encapsulation/incorporation of macromolecular pharmacologically active agents such as proteins, enzymes, peptides, polysaccharides, nucleic acids, cells, tissues, and the like. Immobilization of macromolecular pharmacologically active agents into or onto a finite location of the body can be difficult due to the ease with which some of these macromolecular agents denature when exposed to organic solvents, some constituents present in bodily fluids or to temperatures appreciably higher than room temperature. However, since the method of the present invention, as well as the protein matrix and/or coacervate materials formed by the method described herein utilize biocompatible solvents such as water, DMSO or ethanol, and furthermore does not require heating or utilizes mild heating, the risk of the denaturation of these types of materials is reduced. Furthermore, due to the size of these macromolecular pharmacologically active agents, these agents are encapsulated within the protein matrix and/or biocoacervate upon implantation of stent systems in accordance with the present invention, and thereby are protected from constituents of bodily fluids that would otherwise denature them. Thus, the protein matrix and coacervate devices of the present invention allow these macromolecular agents may exert their therapeutic effects, while yet protecting them from denaturation or other structural degradation.

Cells may also be included in the protein matrix or biocoacervate material of the stent systems of the present invention. Examples of cells which can be utilized as the pharmacologically active agent in the stent system of the present invention include primary cultures as well as established cell lines, including transformed cells. Examples of these include, but are not limited to pancreatic islet cells, human foreskin fibroblasts, Chinese hamster ovary cells, beta cell insulomas, lymphoblastic leukemia cells, mouse 3T3 fibroblasts, dopamine secreting ventral mesencephalon cells, neuroblastold cells, adrenal medulla cells, T-cells combinations of these, and the like. As can be seen from this partial list, cells of all types, including dermal, neural, bone, blood, organ, stem (e.g. multipotent, pluripotent and/or progenitor cells), muscle, glandular, reproductive and immune system cells, as well as cells of all species of origin, can be encapsulated successfully by this method.

Also, other proteins, enzymes, and other agents may be included as pharmacologically active agents in the protein matrix and/or coacervate material utilized in the stent systems of the present invention. Examples of proteins which can be incorporated into the protein-based materials of the present invention include, but are not limited to, hemoglobin, vasporessin, oxytocin, adrenocorticocotrophic hormone, demopressin epidermal growth factor, prolactin, luliberin or luteinising hormone releasing factor, human growth factor, and the like; enzymes such as adenosine deaminase, superoxide dismutase, xanthine oxidase, and the like; enzyme systems; blood clotting factors; clot inhibitors or clot dissolving agents such as streptokinase and tissue plasminogen activator; antigens for immunization; hormones; polysaccharides such as heparin; oligonucleotides; bacteria and other microbial microorganisms including viruses; monoclonal antibodies; vitamins; cofactors; retroviruses for gene therapy, combinations of these and the like.

Furthermore, one embodiment of the present invention includes the incorporation of pancreatic islet cells within the biocompatible protein-based material that surrounds, covers or contacts the one or more stents. The stent system that includes the pancreatic islet cells may be implanted in a vessel wherein the islet cells are in line with the circulatory system to provide an optimum environment for their proper function e.g. insulin production and release in response to blood glucose levels. It is noted that the stent system in this embodiment may include only one stent or may include multiple stents.

An efficacious amount of the aforementioned pharmacologically active agent(s) can easily be determined by those of ordinary skill in the art taking into consideration such parameters as the particular pharmacologically active agent chosen, the size and weight of the patient, the desired therapeutic effect, the pharmacokinetics of the chosen pharmacologically active agent, and the like, as well as by reference to well known resources such as Physicians' Desk Reference®: PDR—52 ed (1998)—Medical Economics 1974. In consideration of these parameters, it has been found that a wide range exists in the amount of the pharmacologically active agent(s) capable of being incorporated into, and subsequently released from or alternatively allowed to exert the agent's therapeutic effects from within, the stent system. More specifically, the amount of pharmacologically active agent that may be incorporated into and then either released from or active from within the protein-based material may range from about 0.001% to about 200%, more preferably, from about 0.05% to about 100%, most preferably from about 0.1% to 70%, based on the weight of the biocompatible protein-based material.

In addition to the biocompatible protein material(s), the biocompatible solvent(s) and pharmacologically active agent(s), the protein-based materials utilized in various embodiments of the present invention advantageously may themselves incorporate other drug delivery devices that would otherwise typically migrate away from the desired delivery site and/or are potentially undesirably reactive with surrounding bodily fluids or tissues. Such migration is undesirable in that the therapeutic effect of the pharmacological agents encapsulated therein may occur away from the desired site, thus eliminating the advantage of localized delivery. When a stent system incorporating a migration-vulnerable and/or reactive drug delivery device (hereinafter referred to as a "two-stage protein based stent system") is subsequently implanted, the migration-vulnerable and/or reactive drug delivery device(s) is/are held in place and protected by the two-stage protein-based materials. More particularly, once implanted and/or administered, the pharmacologically active agent(s) is released by the biodegradable and/or biocompatible material of the migration-vulnerable drug delivery device as it degrades or releases the agent(s). Then the pharmacologically active agents diffuse through the protein-based materials of the two-stage protein-based stent system or is released with the degradation of or diffusion through the protein-based material used in embodiments of the present invention.

Furthermore, the compressed cohesive body or biocoacervate utilized in embodiments of the stent systems of the present invention reduces, if not prevents, the potential for undesirable reaction with bodily fluids or tissues that may otherwise occur upon implantation of a reactive foreign material or device without the protective protein-based material encapsulating or coating such a material or device. It has been shown that the protein-based materials act as a biocompatible, hemocompatible barrier layer that inhibit growth of tissue into the reopened passageways and also act as a wound healing device that can be remodeled and/or resorbed by the host tissue. Examples of such second stage delivery devices subject to migration from the delivery site include, but are not limited to, vesicles, e.g., liposomes, liposheres and microspheres. Vesicles are made up of microparticles or colloidal carriers composed of lipids, carbohydrates or synthetic polymer matrices and are commonly used in liquid drug delivery devices. Vesicles, for example, have been used to deliver anesthetics using formulations with polylactic acid, lecithin, iophendylate and phosphotidyl choline and cholesterol. For a discussion of the characteristics and efficiency of drug delivery from vesicles, see, e.g., Wakiyama et al., *Chem., Pharm. Bull.*, 30, 3719 (1982) and Haynes et al., *Anesthiol*, 74, 105 (1991), the entire disclosures of which are incorporated by reference herein.

Liposomes, the most widely studied type of vesicle, can be formulated to include a wide variety of compositions and structures that are potentially non-toxic, biodegradable and non-immunogenic. Furthermore, studies are in progress to create liposomes that release more drug in response to changes in their environment, including the presence of enzymes or polycations or changes in pH. For a review of the properties and characteristics of liposomes see, e.g., Langer, *Science*, 249, 1527 (1990); and Langer, *Ann. Biomed. Eng.*, 23, 101 (1995), the entire disclosures of which are incorporated by reference herein.

Liposheres are an aqueous microdispersion of water insoluble, spherical microparticles (from about 0.2 to about 100 um in diameter), each consisting of a solid core of hydrophobic triglycerides and drug particles that are embedded with phospholipids on the surface. Liposheres are disclosed in U.S. Pat. No. 5,188,837, issued to Domb, the disclosure of which is incorporated herein by reference.

Microspheres typically comprise a biodegradable polymer matrix incorporating a drug. Microspheres can be formed by a wide variety of techniques known to those of skill in the art. Examples of microsphere forming techniques include, but are not limited to, (a) phase separation by emulsification and subsequent organic solvent evaporation (including complex emulsion methods such as oil in water emulsions, water in oil emulsions and water-oil-water emulsions); (b) coacervation-phase separation; (c) melt dispersion; (d) interfacial deposition; (e) in situ polymerization; (f) spray drying and spray congealing; (g) air suspension coating; and (h) pan and spray coating. These methods, as well as properties and characteristics of microspheres are disclosed in, e.g., U.S. Pat. Nos. 4,652,441; 5,100,669; 4,526,938; WO 93/24150; EPA 0258780 A2; U.S. Pat. Nos. 4,438,253; and U.S. Pat. 5,330, 768, the entire disclosures of which are incorporated by reference herein.

Inasmuch as the migration-vulnerable and/or-reactive drug delivery devices will desirably further encapsulate a pharmacologically active agent, the amount of these devices to be utilized in the two-stage protein-based stent systems of the present invention may be determined by the dosage of the pharmacologically active agent, as determined and described hereinabove. Inasmuch as such migration-vulneiable and/or reactive drug delivery devices represent solid matter that may change the ability of the coatable composition to be coated or included in the coacervate material, the amount of such devices to be included in a two-stage protein-based stent system desirably ranges about 10,000 to about 1 billion, more preferably ranges from about 1 million to about 500 million, and most preferably ranges from about 200 million to about 400 million.

Additionally, the stent systems formed according to the method of the present invention may optionally include one or more additives added to the protein-based materials. Such additives may be utilized, for example, to facilitate the processing of the stent systems, to stabilize the pharmacologically active agents, to facilitate the activity of the pharmacologically active agents, or to alter the release characteristics of the protein matrix device. For example, when the pharmacologically active agent is to be an enzyme, such as xanthine oxidase or superoxide dismutase, the protein matrix device may further comprise an amount of an enzyme substrate, such as xanthine, to facilitate the action of the enzyme.

Additionally, hydrophobic substances such as lipids can be incorporated into the stent system as additives to extend the duration of drug release, while hydrophilic, polar additives, such as salts and amino acids, can be added to facilitate, i.e., shorten the duration of, drug release. Exemplary hydrophobic substances include lipids, e.g., tristearin, ethyl stearate, phosphotidycholine, polyethylene glycol (PEG); fatty acids, e.g., sebacic acid, erucic acid; combinations of these and the like. A particularly preferred hydrophobic additive useful to extend the release of the pharmacologically active agents comprises a combination of a dimer of erucic acid and sebacic acid, wherein the ratio of the dimer of erucic acid to sebacic acid is 1:4. Exemplary hydrophilic additives useful to shorten the release duration of the pharmacologically active agent include but are not limited to, salts, such as sodium chloride; and amino acids, such as glutamine and glycine. If additives are to be incorporated into the coatable composition, they will preferably be included in an amount so that the desired result of the additive is exhibited.

Additionally, other additives, such as one or more polymeric materials, may be included in the coatable composition to add or enhance the features of the stent system. For example, one or more polymeric materials may be utilized to provide additional strength and/or elasticity to the stent system or provide for an increase or decrease of the release of pharmacologically active agents. Examples of biodegradable and/or biocompatible polymeric materials suitable for use in the drug delivery device of the present invention include, but are not limited to, epoxies, polyesters, acrylics, nylons, silicones, polyanhydride, polyurethane, polycarbonate, poly(tetrafluoroethylene) (PTFE), polycaprolactone, polyethylene oxide, polyethylene glycol, poly(vinyl chloride), polylactic acid, polyglycolic acid, polypropylene oxide, poly(akylene) glycol, polyoxyethylene, sebacic acid, polyvinyl alcohol (PVA), 2-hydroxyethyl methacrylate (HEMA), polymethyl methacrylate, 1,3-bis(carboxyphenoxy)propane, lipids, phosphatidylcholine, triglycerides, polyhydroxybutyrate (PHB), polyhydroxyvalerate (PHV), poly(ethylene oxide) (PEO), poly ortho esters, poly(amino acids), polycynoacrylates, polyphophazenes, polysulfone, polyamine, poly(amido amines), fibrin, graphite, flexible fluoropolymer, isobutyl-based, isopropyl styrene, vinyl pyrrolidone, cellulose acetate dibutyrate, silicone rubber, copolymers of these, and the like.

Other materials that may be incorporated into the matrix as additives that are not considered polymers, but provide enhanced features include, but are not limited to, glycerin, ceramics, bioceramics, glasses bioglasses, glass-ceramics, resin cement, resin fill; more specifically, glass ionomer, hydroxyapatite, calcium sulfate, $Al_2O_3$, tricalcium phosphate, alginate, carbon, hyaluronic acid, calcium phosphate salts, sugars, lipoproteins, starches, ferrous salts and compounds, carbohydrates, salts, polysaccharides, magnetic particles, fibers or other magnetic substances, mucoadhesive enhancers such as glycerol and alginate, absorption or membrane permeation enhancers such as ascorbic acid, citric acid and Lauroylcarnitine. Additional other materials that may be incorporated into the matrix included alloys such as, cobalt-based, galvanic-based, stainless steel-based, titanium-based, zirconium oxide, zirconia, aluminum-based, vanadium-based, molybdenum-based, nickel-based, iron-based, or zinc-based (zinc phosphate, zinc polycarboxylate).

Generally, the amount of additives may vary between from about 0% to about 300%, preferably from about 100% to 200% by weight, based upon the weight of the biocompatible protein material.

Manufacturing stent systems with the method of the present invention imparts many advantageous qualities to the resulting stent systems. First of all, the resulting stent system is substantially cohesive and durable, i.e., with a solvent content of from about 10% to about 60%, preferably of from about 30% to about 50%. Thus, administration of the stent system is made easy, inasmuch as it may be easily handled to be injected or implanted. Furthermore, once injected or implanted, some embodiments of the biocompatible protein-based material may absorb water and swell, thereby assisting the stent system to stay substantially in the location where it was implanted or injected. Also, the components and the amounts thereof to be utilized in the stent system may be selected so as to optimize the rate of delivery of the pharmacologically active agent depending upon the desired therapeutic effect and pharmacokinetics of the chosen pharmacologically active agent.

Also, since biocompatible solvents are used in the manufacture of the stent systems, the potential for adverse tissue reactions to chemical solvents are reduced, if not substantially precluded. For all of these reasons, stent systems in accordance with the present invention may advantageously be used to effect a local therapeutic result in a patient in need of such treatment. The stent system may be delivered to a site within a patient to initiate a therapeutic effect either locally or systemically. Depending on the desired therapeutic effect, the stent systems may be used to regenerate tissue, repair tissue, replace tissue, and deliver local and systemic therapeutic agents such as restenosis inhibitors, analgesia or anesthesia, or alternatively, may be used to treat specific conditions, such as coronary artery disease, peripheral blood vessel disease, heart valve failure, bronchial tube damage, airway damage, diabetes, neurovasculature afflictions, aneurisms, provide support to weakened structures (e.g. heart valves, venous valves, heart wall, nasal sinuses, arteries, urinary tracts, reproductive tracts, airways, digestive tracts, ear canal) and other tissue specific conditions. Stent systems that include pharmacologically active agents may be utilized in instances where long term, sustained, controlled release of pharmacologically active agents is desirable.

Furthermore, the stent systems of the present invention may incorporate multiple pharmacologically active agents, one or more of which may be agents that are effective to suppress an immune and/or inflammatory response. In this regard, the stent systems will deter, or substantially prevent the encapsulation or formation of scar tissue that typically occurs when a foreign body is introduced into a host. Such encapsulation or fibrous tissue formation could potentially have the undesirable effect of limiting the efficacy of the stent system.

In another embodiment of the present invention the stent system may utilize a biocoacervate material rather than or in combination with the previously described protein matrix material. In general, the biocoacervates, utilized in various embodiments of the present invention generally include one or more proteins, one or more glycosaminoglycans, proteoglycans or mucopolysaccharides and one or more biocompatible solvents. Also, the biocoacervates may include one or more pharmacologically active agents and/or one or more additives to provide a therapeutic agent or enhance the properties desired from the material. Any of the proteins, solvents, pharmacologically active agents and additives listed above may be used in producing the biocoacervate. However, it is noted that generally the proteins are soluble or are solubilized and have an affinity to bind with proteoglycans. The proteins used thereby include functional groups that attract and retain the proteoglycans. In many embodiments of the present invention, the biocoacervates include water-absorbing, biocompatible proteins. The utilization of a water-absorbing biocompatible protein included in the biocoacervate provides the advantage that, not only will the biocoacervates be bioresorbable, but may remodel to mimic and support the tissue it contacts. That is, the metabolites of any degradation and/or resorption of the water-absorbing biocompatible protein may be reused by the patient's body rather than excreted.

As previously indicated, the biocoacervates utilized in various embodiments of the present invention also include one or more glycosaminoglycans, proteoglycans or mucopolysaccharides. Examples of proteoglycans that are utilized in the coacervates and biomaterials of the present invention include but are not limited to heparin, heparin sulfate, heparan, dermatin, dermatin sulfate, heparin-hyaluronic acid, chondroitin, chondroitin sulfate, hyaluronic acid, aggrecan, decorin, biglycan, fibromodulin, lumican, combinations, proteoglycan complexs or compounds and the like.

It is also noted that the additives may be added at any time during the preparation of the coacervate or to a subsequently formulated biomaterial. For example additives, such as particles (drugs, proteins . . . ), macromolecules (DNA, proteins, peptides . . . ), small molecules (NSAIDS, Sufentanil, capsaicin . . . ), combininations thereof and the like may be added to the protein solution or may be added to the molten coacervate. For example, additives, such as polyethylene glycol, hydroxy appetite and glycerol may be added during the formation of the coacervate, may be added to the coacervate in a melted state or could be loaded into a coacervated following stabilization by a crosslinking agent. Such addition techniques has the benefit of distributing the additive homogeneously throughout the coacervate or biomaterial. If additives are to be incorporated into the coacervates or biomaterials of the present invention, they will preferably be included in an amount so that the desired result of the additive is exhibited. Generally, if additives are included, the amount of additives may vary between from about 0.05% to about 300%, preferably from about 2% to 200% by weight, and most preferably from about 5% to 50% by weight based upon the weight of the biocompatible protein material.

Figure 4:
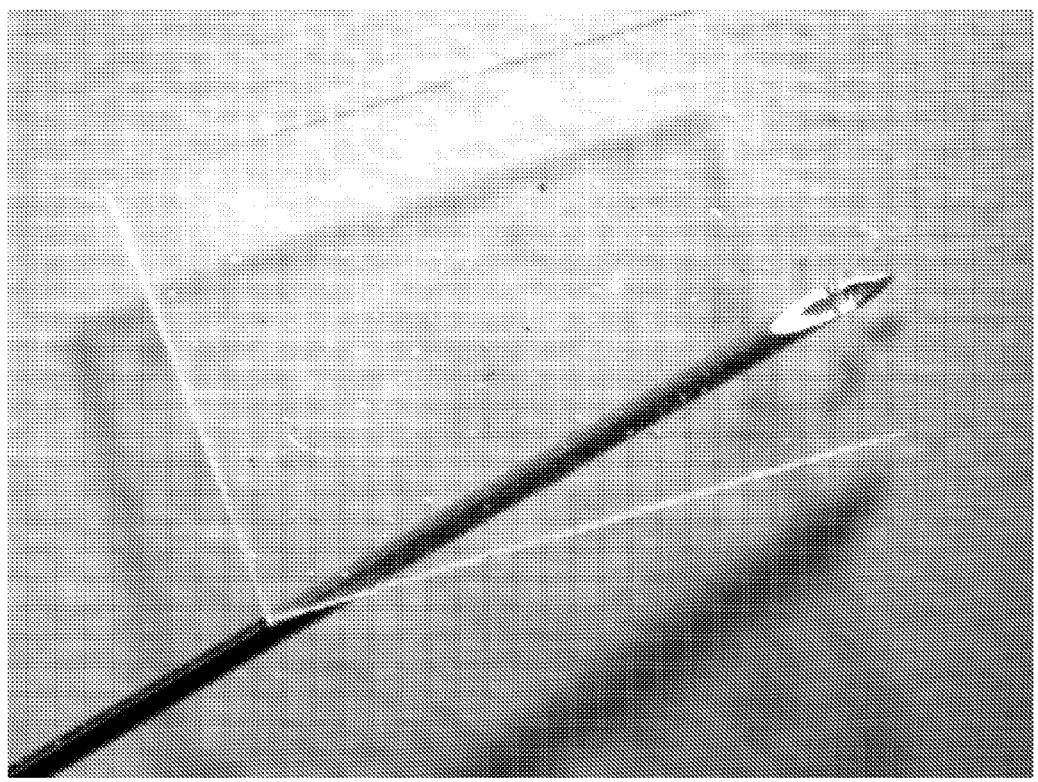
FIG. 4 depicts one embodiment of the biocoacervate of the present invention cut into a square shape.

One method of producing the coacervate of the present invention is by providing one or more selected soluble or solubilized primary proteins, such as collagen or fibronectin and optionally one or more soluble or solubilized secondary proteins such as elastin or albumin. Generally, the primary proteins are proteins that have a plurality of glycosaminoglycans, proteoglycans or mucopolysaccharides binding sites. The primary and secondary proteins are added to a sufficient amount of biocompatible solvent, preferably water, under heat until the proteins are substantially dissolved in the solvent. The proteins are added to the solvent that is generally heated to approximately 20-150° C., preferably 40-90° C., and most preferably 40-60° C. thereby producing a protein solution. Once the protein solution is formed, one or more proteoglycans, such as heparin or chondroitin sulfate are minimally mixed with the protein solution. Upon adding the proteoglycan to the heated solution containing the primary and secondary proteins a protein body falls out. The protein body generally falls out of the solution as an amorphous gelatin-like material allowing it to be extracted from the solution. It is noted that before adding the one or more proteoglycans to the protein solution one or more other materials (pharmacologically active agents, additives, etc.) may be added to the one or more heated solvents (water) while stirring. Once extracted from the solution, the gelatin-like material is allowed to cool thereby forming a cohesive elastic coacervate, The solution and coacervate are normally allowed to cool to between 0-35° C., preferably 10-25° C., most preferably 17-22° C. and the solution is poured off the coacerate or the coacervate is extracted from the solution. It is noted that the cooled, extracted material has elastic mechanical properties similar to the material utilized in the rubberbands. Various embodiments of the formed biocoacervate may be reformed into any shape and size by simply heating the biocoacervate until it melts and forms a liquid. Generally, the biocoacervate can be melted at a temperature between 20-120° C., preferably 25-80° C., most preferably 30-65° C. Next, the biocoacervate may be poured into a mold and allowed to cool or allowed to reform into a solid outside of a mold, thereby reforming into the desired shape and size. FIG. 4 depicts the biocoacervate of the present invention cut into a square shape.

It is noted that in forming the protein solution, the primary and secondary proteins, the biocompatible solvent(s), and optionally the pharmacologically active agent(s) and additive(s) may be combined in any manner. For example, these components may simply be combined in one step, or alternatively, the primary and secondary protein materials may be dissolved in a biocompatible solvent and an additional protein material, pharmacologically active agent and/or additive may be dissolved and/or suspended in the same or another biocompatible solvent and then the resulting two solutions are mixed.

Preferably, the biocompatible solvent comprises water. The amount of biocompatible solvent utilized in the formation of the coacervate utilized in embodiments of the present invention will preferably be that amount sufficient to result in the primary and secondary proteins being fluid and flowable enough to allow the protein to enter into solution. Generally, the amount of biocompatible solvent suitable for use in the method of the present invention will range from about 100% to about 50,000%, preferably from about 500% to about 10,000% by weight, and more preferably from about 500% to about 2000% by weight, based upon the weight and/or amount of the protein utilized.

Once the coacervate is formed, it may be optionally compressed to further form, modify, set the configuration and/or remove any excess solvent or air trapped within the biocoacervate. The compression may also be performed when a melted coacervate is resetting to a solid state. The compression steps may be utilized to form a stent system by placing the coacervate and stent into a compression chamber and forming the coacervate over the stent by applying compression. Any manually or automatically operable mechanical, pneumatic, hydraulic, or electrical molding device capable of subjecting the coacervate to pressure is suitable for use in the method of the present invention. An example of such a compression device is described above. In the production of various embodiments of the present invention, a molding device may be utilized that is capable of applying a pressure of from about 100 pounds per square inch (psi) to about 100,000 psi for a time period of from about 2 seconds to about 48 hours. Preferably, the molding device used in the method of the present invention will be capable of applying a pressure of from about 1000 psi to about 30,000 psi for a time period of from about 10 seconds to about 60 minutes. More preferably, the molding device used in the method of the present invention will be capable of applying a pressure of from about 3,000 psi to about 25,000 psi for a time period of from about one minute to about ten minutes.

The biocoacervate of the present invention is generally not soluble in water at room temperature. However, the coacervate may be dissolved in hypertonic saline solution or other physiological solutions. A biomaterial that does not dissolve in hypertonic solution or other physiological solutions may be produced from the biocoacervate by setting or stabilizing the biocoacervate in a desired configuration and size by utilizing a crosslinking technique.

Embodiments of the stent system utilizing either a compressed protein matrix or a biocoacervate may be crosslinked by reacting the components of the protein matrix or coacervate with a suitable and biocompatible crosslinking agent. Crosslinking agents that may be utilized to stabilize a protein matrix or coacervate include, but are not limited to glutaraldehyde, p-Azidobenzolyl Hydazide, N-5-Azido-2-nitrobenzoyloxysuccinimide, 4-[p-Azidosalicylamido]butylamine, any other suitable crosslinking agent and any combination thereof. A description and list of various crosslinking agents and a disclosure of methods of performing crosslinking steps with such agents may be found in the Pierce Endogen 2001-2002 Catalog which is hereby incorporated by reference.

Furthermore, it is noted that embodiments of the stent system of the present invention may include crosslinking reagents that may be initiated and thereby perform the crosslinking process by UV light activation or other radiation source, such as ultrasound, E-Beam or gamma ray or any other activation means.

The protein matrix or coacervate may be crosslinked by utilizing methods generally known in the art. For example, a protein matrix may be partially or entirely crosslinked by exposing, contacting and/or incubating the stent system with a gaseous crosslinking reagent, liquid crosslinking reagent, light or combination thereof. In one embodiment of the present invention a tube may be crosslinked on the outside surface by exposing only the outside surface to a crosslinking reagent, such as glutaraldehyde. Such a matrix or a biomaterial formed from a coacervate has the advantages of including an outer exterior that is very pliable and possesses greater mechanical characteristics, but includes an interior surface that retains higher biofunctional features. For example, cell growth may be controlled on portions of the protein matrix or biomaterial by exposing such areas to crosslinking reagents while still having portions of the same protein matrix that are not crosslinked, and thereby producing biofunctional selective features for the entire stent system. For example crosslinking portions of the protein matrix or coacervate may be used to change, modify and/or inhibit cell attachment. It is also noted that the pharmacologically active agent may also be crosslinked, bonded and/or chemically and/or physically linked to protein matrix or biocoacervate either partially or in totality. For example, glutaraldehyde may cross-link heparin to a single surface of a protein matrix device.

Embodiments of the present invention may include the addition of reagents to properly pH the resulting stent system and thereby enhance the biocompatible characteristics of the device with the host tissue of which it is to be administered and/or to enhance the production of the protein-base materials. When preparing the protein matrix or biomaterial device, the pH steps of the biocompatable material and biocompatable solvent may occur prior to the partial drying preparation of the cohesive body or during the formation of the coacervate. The pH steps can be started with the addition of biocompatable solvent to the protein material or to the mixture of protein material and optional biocompatible materials, or the pH steps can be started after mixing the material(s) and solvent(s) together before the cohesive body or biocoacervate is formed. Alternatively, the pH steps may occur after the formation of the cohesive body or in the melted phase of a formed coacervate by simply adding a pH modifier to the cohesive body or melted coacervate. In one embodiment, the pH steps can include the addition of drops of 0.05N to 4.0N acid or base to the solvent wetted material until the desired pH is reached as indicated by a pH meter, pH paper or any pH indicator. More preferably, the addition of drops of 0.1N-0.5 N acid or base are used. Although any acid or base may be used, the preferable acids and bases are HCl and NaOH, respectively. If known amounts of biocompatable material are used it may be possible to add acid or base to adjust the pH when the biocompatable material is first wetted, thereby allowing wetting and pH adjustments to occur in one step.

The patient to which the stent system is administered may be any patient in need of a therapeutic treatment. Preferably, the patient is a mammal, reptiles or birds. More preferably, the patient is a human. Furthermore, the stent system can be implanted in any location to which it is desired to effect a local therapeutic response.

Figure 5:
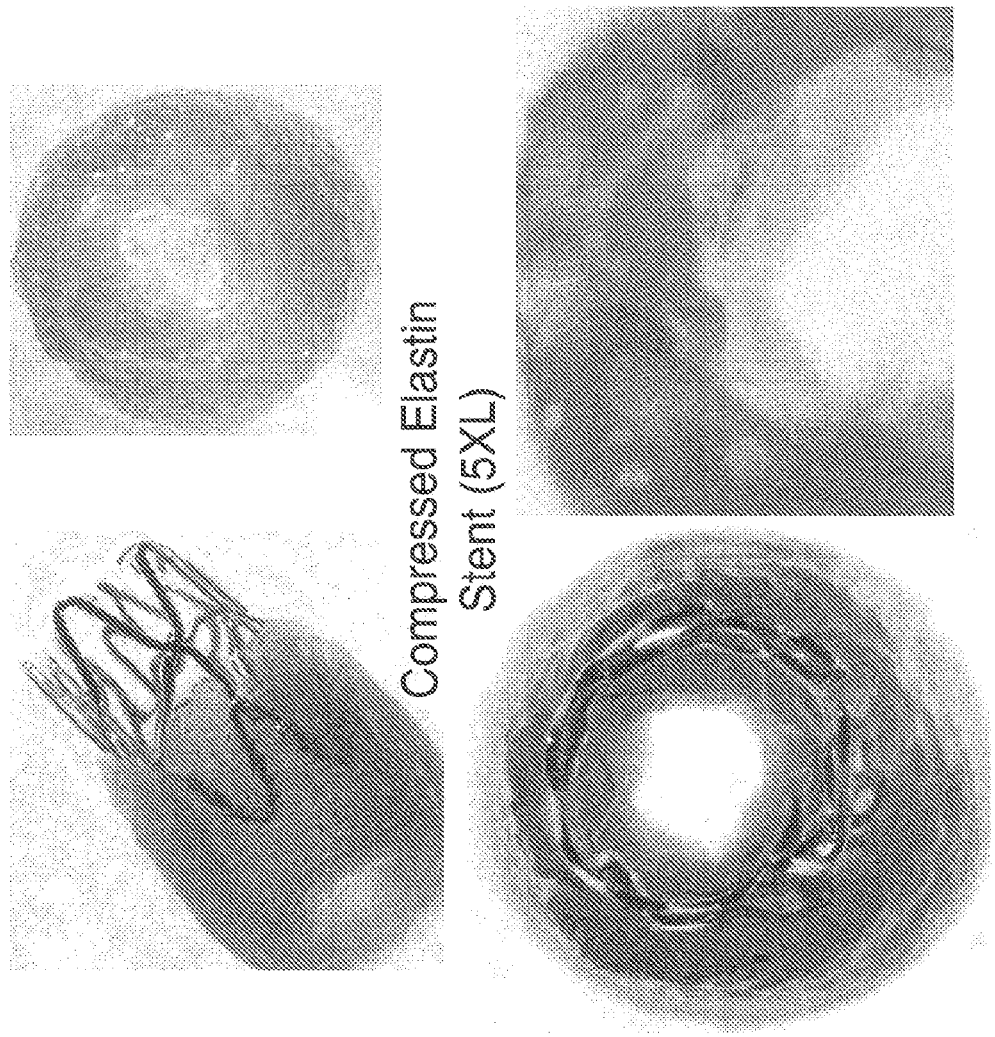
FIGS. 5-7 depict various embodiments of encapsulated stents that may be utilized in the stent systems of the present invention.
Figure 6:
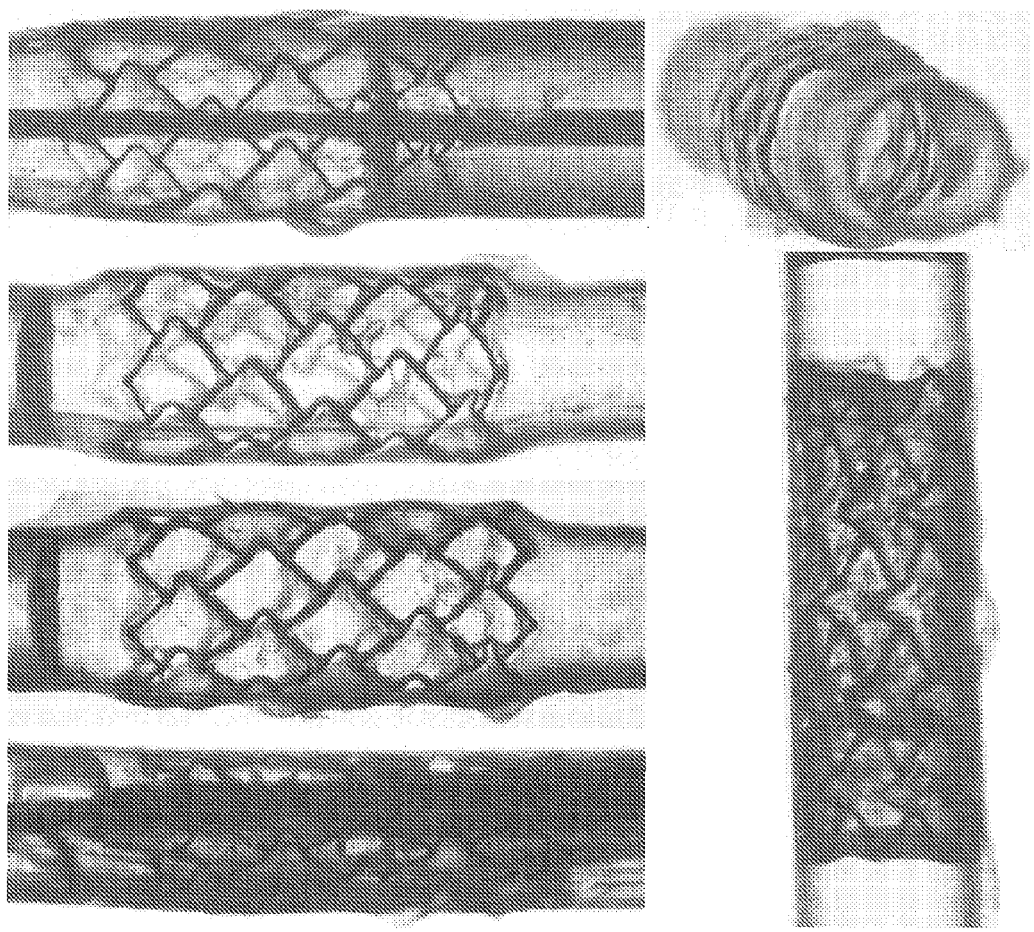
Figure 7:
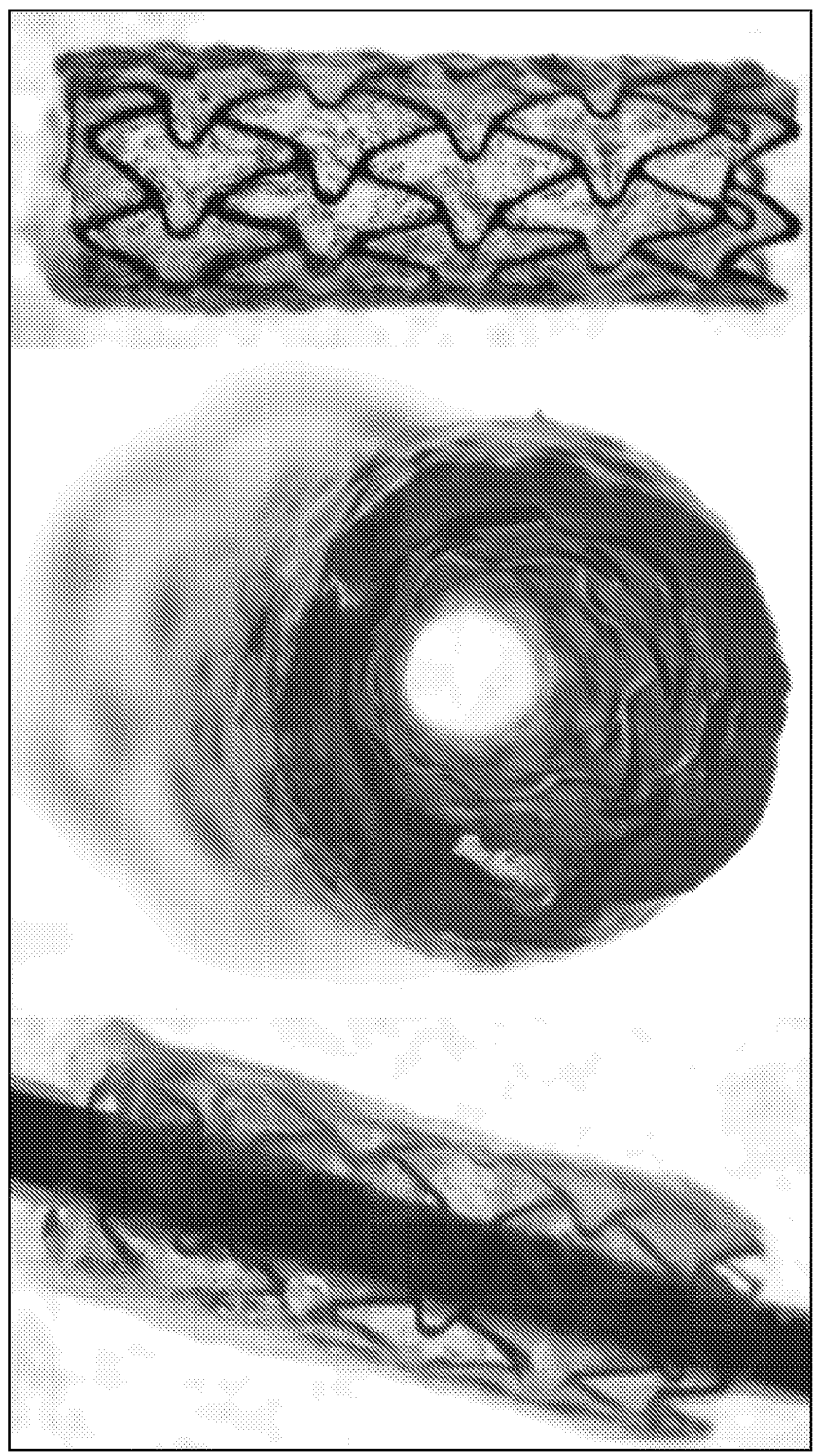

All types of stents, including those known in the art, may be utilized in association with the present invention. Generally, a stent is a tube made of metal or plastic that is inserted into a vessel or passage to keep the lumen open and prevent closure due to a stricture or external compression. Other stent embodiments may be a plastic or metal mesh structure. An example of a mesh stent encapsulated in a protein matrix material is depicted in FIGS. 5-7. Other mesh stents may be produced from plastics or fibers, such as PTFE, polypropylene, polyethylene, silk cotton and the like. As depicted one or more of such mesh stents may be encapsulated, embedded or attached to a tube of protein matrix material or biocoacervate material.

Stents are commonly used to keep blood vessels open in the coronary arteries, into the oesophagus for strictures or cancer, the ureter to maintain drainage from the kidneys, or the bile duct for pancreatic cancer or cholangiocarcinoma. Stents are also commonly utilized in other vascular and neural applications to keep blood vessels open and provide structural stability to the vessel. Embodiments of the current invention may also be used to provide support to weakened structures (e.g. heart valves, venous valves, heart wall, nasal sinuses, arteries, urinary tracts, reproductive tracts, airways, digestive tracts, ear canal). Embodiments of the present invention may also be utilized as vessel grafts. Stents are usually inserted under radiological guidance and can be inserted percutaneously. Stents are commonly made of gold, nitinol, stainless steel or various plastics. Gold is considered more biocompatible. However, stents constructed with any suitable material may be utilized with the protein matrix or biocoacervate in various embodiments of the present invention. Once example of a stent that may be utilized with the present invention includes weaved materials or braided materials such as metals (e.g. nitinol), plastics (e.g. polypropylene, polyethylene, PTFE, polyester) and fibers (e.g. cotton, silk).

Encapsulation or coating of one or more stents with the protein matrix material or coacervate of the present invention produces a device that is more biocompatible with the host tissue than the stent alone. Such encapsulation, embedding, attaching or coating of the stent reduces or prevents adverse immuno-response reactions to the stent being administered and further enhances acceptance and remodeling of the stent system by the host tissue.

Figure 8:
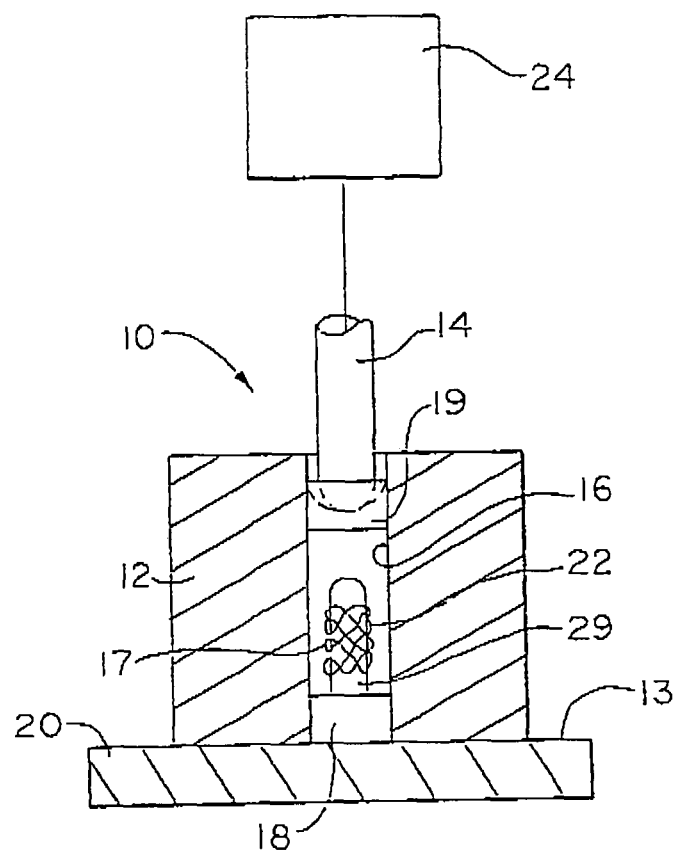
FIG. 8 is a schematic illustration, in partial cross-sectional view, of a compression molding device that may be used in the method of the present invention in wherein the inner insert includes a mandrel that that is engaged with a stent.

The protein matrix material or biocoacervate may completely encapsulate or otherwise coat the exterior of the one or more stents. Generally, the encapsulated or coated stent system is made in a similar process as described above. FIG. 8 depicts a compression molding device wherein the inner insert 18 includes a mandrel 29 that extends upward from the insert 18 into the chamber 17. Pursuant to one method of preparation, following preparation of the cohesive body 23 or coacervate (not shown), inner insert 18 is inserted into the cavity 16. A stent 32 is next positioned over the mandrel 29 and the cohesive body 22 is placed in the cavity and compressed. If the coacervate is utilized, the coacervate may be melted, placed in the cavity, allowed to cool to reform and subsequently compressed. Encapsulation or coating of the stent 32 is determined by the size of the mandrel 29 utilized in the compression molding device. A stent 32 that fits snuggly over the mandrel 29 will allow for only a coating upon the exterior of the stent 32. A smaller mandrel 29 that does not provide as snug a fit for the stent 32 will allow protein matrix material to move between the mandrel 29 and the stent 32 thereby creating an encapsulation of the stent 32. The encapsulated or coated stent device is then removed from the compression molding device in a similar way as described above and shown in FIG. 3. The stent device, either encapsulated or coated generally has a wall thickness of approximately 0.05 mm to 2 mm and preferably has a wall thickness of 0.15 to 0.50 mm. It is noted that a stent 32 may be coated with the melted biocoacervate by utilizing a number of other techniques including, but not limited to, spray coating, dip coating and the like.

As previously described additional polymeric and other biocompatible materials may be included in the protein matrix material to provide additional structural stability and durability to the encapsulated or coated stent device. Also, other structural materials, such as proteoglycans, can be used in this process to add greater tissue imitation and biocompatibility. In various embodiments, the proteoglycans can replace or be mixed with the protein material in the production of the protein matrix material.

Additionally, as previously described, the protein matrix material or coacervate biomaterial included in the encapsulated or coated stent cover may be cross-linked to provide additional desirable features such as the inhibition of cell growth or to provide additional structural durability and stability. For example the protein matrix material of the encapsulated or coated stent device may be crosslinked by contacting the material with a chemical reagent, such as glutaraldehyde, or other type of crosslinking reagent. FIG. 7 depicts various views of a tube made of collagen, elastin and heparin that has been crosslinked by being exposed to a 1% solution of glutaraldehyde for 5 minutes. FIGS. 5 and 6 are additional examples that depict additional embodiments of encapsulated and coated stents. FIG. 5 depicts an encapsulated stent device including a protein matrix material comprising a 1:1 ratio of elastin to albumen (bovine serum albumin).

Other embodiments of the stent device of the present invention may be produced by preparing a stent device that includes a ratio of 2:1:2 collagen to elastin to albumen, 4:1 collagen to elastin, 1:4:15 heparin to elastin to collagen, 1:4:15 condroitin to elastin to collagen. Each embodiment depicted in the Figures illustrates the uniform distribution of the protein matrix material around the stent and also has been tested to show the strength and durability of the stent after expansion by a balloon.

Furthermore, the stent devices can also be used to incorporate peptides and other pharmacologically active agents that have the ability to inhibit cell migration. A disadvantage of utilizing stents in a vessel is that the expansion of the vessel upon insertion of stent weakens the vessel and may allow smooth muscle cells to enter into the vessels thereby occluding or restinosing the vessel. Occlusion of the vessel and restinosis can be treated by utilizing the stent device and vessels or tube grafts of the present invention. It is important to note that inserting a stent with or without drugs can prevent such breakdown and growth of cells into the diseased or damaged vessel.

Embodiments of the protein matrix covered stent system may include other materials already covering one or more of the stents, e.g., teflon, PTFE, ePTFE, plastics, and gels. Furthermore, in some of the embodiments of the stent system at least one other stent may be uncovered. The configuration could be that protein matrix material or biocoacervate is placed around the other material or that the protein matrix material encases the other material used for covering the stent. The protein matrix material may either be encasing the stent or it may be sandwiched between multiple stents. The covered stent will reduce the amount of plaque that gets into the bloodstream after balloon angioplasty.

The following are examples of various stent embodiments that may be utilized in the stent systems of the present invention. It is noted that these examples are not intended to limit the scope of the application wherein any stent coated or encapsulated with the protein matrix or biocoacervate is contemplated as a part of the present invention. However, the following embodiments may also be considered in combination with other types of coating or encapsulation materials.

One embodiment of the present invention includes single strand stents. Single strand stents generally include a single strand of a suitable material, such as gold, nitinol, stainless steel biodegradable polymers, plastic and combinations thereof, that is shaped to provide a structural scaffolding, which supports the walls of the host tissue surrounding it. In various embodiments, the single strand stents are encapsulated in a protein matrix or biocoacervate material to form a tube. However, simple coating of the single strand stent is also considered. FIGS. 9a-b, 10a-b, 11a-b, 12 and 13 depict a few embodiments of the single strand stents. Generally, the single strand stents utilized in the present invention may include metallic or polymeric spring, ring or any wire shape support that collapses for insertion into a catheter and then expands when deployed from the catheter to hold the stent against the blood vessel wall. The spring, ring or wire may be made out of any suitable material, such as gold, nitinol, stainless steel, polymeric material or rubber. The material in these various embodiments may also be biodegradable and/or bioresorbable. The spring, ring or wire is generally made so that it can collapse on its side and elongate to reduce its size so as to fit within a delivery catheter. As previously suggested, one or more springs, rings or wire stents can be completely encapsulated within a tube structure of protein matrix material or coacervate biomaterial. The encapsulated spring, ring or wire stent can be reduced in size so that it fits within a catheter assembly without the use of a balloon to deploy it. The encapsulated spring, ring or wire stent assembly can be reduced in size to fit within a delivery catheter that only needs to be freed from the catheter. After the protein matrix material spring, ring or wire stent is freed from the catheter the spring, ring or wire stent will open with greater force than a tube without the spring, ring or wire stent. The spring, ring or wire stent will add greater force against the vessel wall to hold the protein matrix or coacervate material securely in place.

Figure 9A:
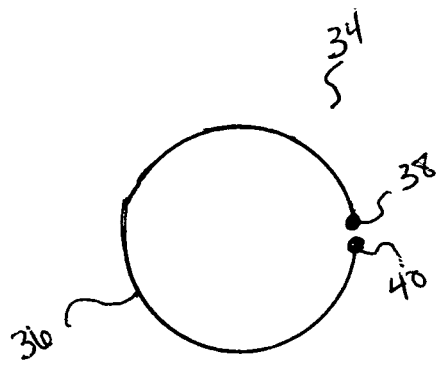
FIG. 9a is a front view of one embodiment of a single strand stent that has a helical configuration.
Figure 9B:
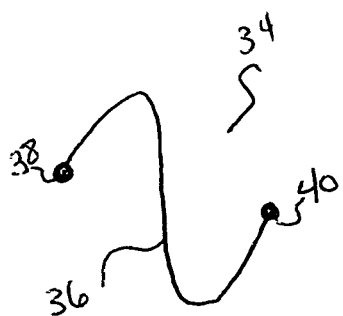
FIG. 9b is a side view of one embodiment of a single strand stent that has a helical configuration.
Figure 9C:
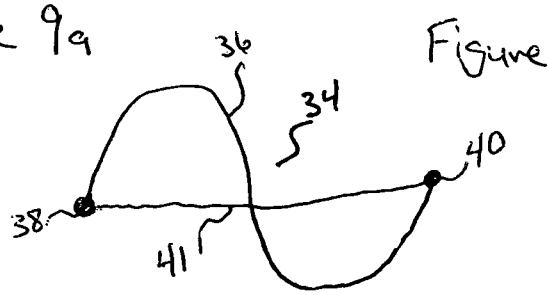
FIG. 9c is a side view of one embodiment of a single strand stent that has a helical configuration wherein the ends are joined by a joining member.

FIGS. 9a-16 depict metallic or polymeric springs, rings or wires in the shape of a loop (e.g., part of spring, shape of letter o, c or e where the tails go in different directions and come close to forming an e or o when looked at from a side perspective viewpoint). The single strands are generally configured to perform one or more loops around the lumen or passageway. FIGS. 9a and 9b depict one embodiment of a single strand stent 34 that may be utilized as a loop strut for maintaining the clearance of a passageway. The single strand stent 34 of FIGS. 9a and 9b generally includes a single strand 36 that is twisted in a single helix configuration and includes a blunt distal end 38 and proximal end 40. FIG. 9a depicts a front view of the single strand stent 36 in a helical configuration that illustrates the open loop strut configuration, which provides an open lumen for the passageway. FIG. 9b depicts the side view of the same single strand stent 34 depicted in FIG. 9a. Finally, FIG. 9c illustrates another embodiment of the helical stent 34 wherein the proximal and distal ends, 38, 40 are joined with a joining member 41. The joining member 41 may be a single strand similar to the type utilized to produce the helical stent 34 or may be made of a material different than the helical stent 34.

Figure 10A:
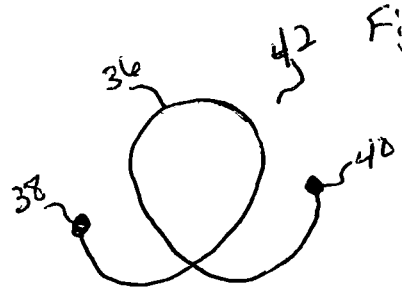
FIG. 10a is a front view of one embodiment of a single strand stent that has an "e" configuration.
Figure 10B:
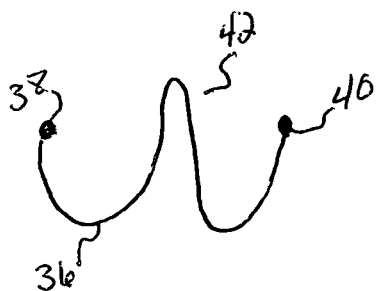
FIG. 10b is a side view of one embodiment of a single strand stent that has an "e" configuration.

FIGS. 10a-b depicts another embodiment of a single strand stent of the present invention. The single strand stent 42 depicted in FIGS. 10a and 10b are shaped in an "e" configuration. The e-stent 42 generally include a single strand 36 that is twisted in an "e" shape configuration and includes a blunt distal end 38 and proximal end 40. FIG. 10a depicts a front view of the single strand stent 42 in the "e" configuration and illustrates the open loop strut configuration, which provides an open lumen for the passageway. FIG. 10b depicts the side view of the same single strand stent 42 depicted in FIG. 10a.

Figure 11A:
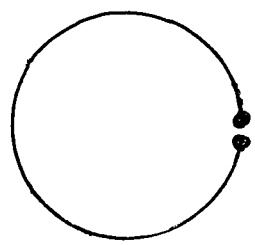
FIG. 11a is a front view of one embodiment of a single strand stent that has a figure eight configuration.
Figure 11B:
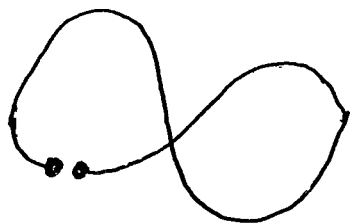
FIG. 11b is a side view of one embodiment of a single strand stent that has a figure eight configuration.

FIGS. 11a-b depicts another embodiment of a single strand stent of the present invention. The single strand stent 44 depicted in FIGS. 11a and 11b are shaped in a "figure eight" configuration. The eight-stent 44 generally include a single strand 36 that is twisted in a "figure eight" shape configuration and includes a blunt distal end 38 and proximal end 40. Optionally, the distal and proximal ends 38, 40 may be joined to form an eight-stent 44 that has a continuous strand 36 (not shown). FIG. 11a depicts a front view of the single strand stent 44 in the "figure eight" configuration and illustrates the open loop strut configuration, which provides an open lumen for the passageway. FIG. 11b depicts the side view of the same single strand stent 44 depicted in FIG. 11a.

Figure 12:
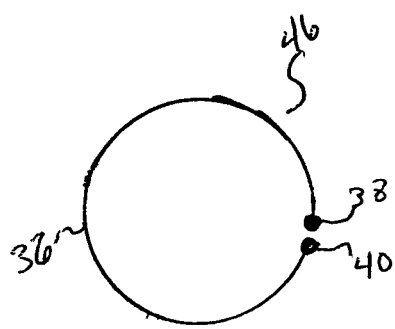
FIG. 12 is a front view of one embodiment of a single strand stent that has an o-ring configuration.
Figure 13:
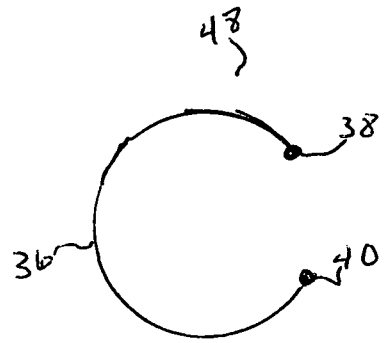
FIG. 13 is a front view of one embodiment of a single strand stent that has a c-ring configuration.
Figure 14:
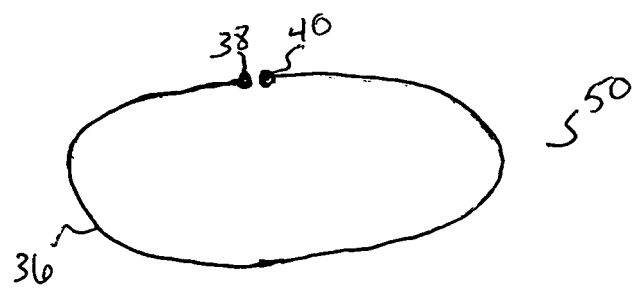
FIG. 14 is a front view of one embodiment of a single strand stent that has an oval-ring configuration.
Figure 17:
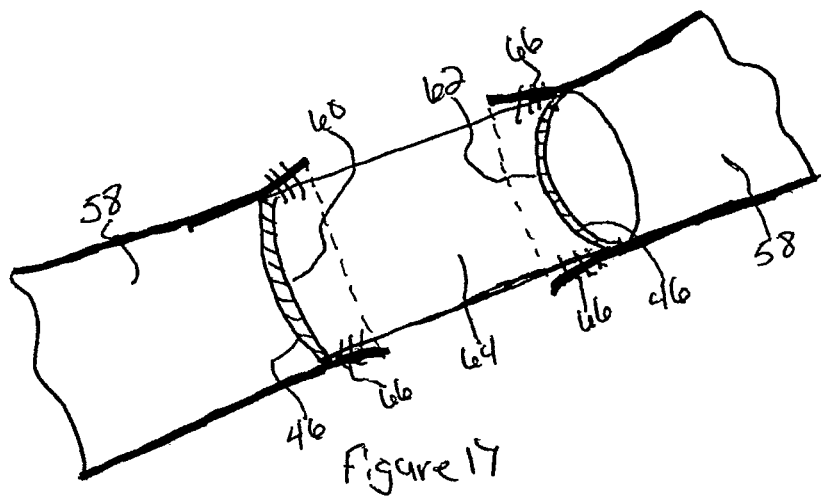
FIG. 17 is a perspective view of one embodiment of a vessel graft including an o-ring at each end of the graft.

Other additional single strand stent embodiments include the utilization of two or more o-rings, c-rings or oval-rings. FIGS. 12-14 disclose embodiments of such an o-ring 46, c-ring 48 and oval-ring 50. Generally the o-ring 46, c-ring 48 and oval-ring 50 include a single strand 36 that is rounded into an "o" configuration and includes a blunt distal end 38 and proximal end 40. Optionally, the distal and proximal ends 38, 40 may be joined to form an o-ring, c-ring or oval-ring stent 46, 48, 50 that has a continuous strand (not shown). FIGS. 12-14 depict front views of the single strand stents 46, 48 and 50 in the "o-ring", "c-ring" and oval-ring configuration and illustrates the open loop strut configuration, which provides an open lumen for the passageway. It is noted that generally, two or more o-rings, c-rings and/or oval-rings are utilized in various embodiments of the present invention. For example, an o-ring or c-ring can be encapsulated on each end of a tube made of the above described protein matrix or biocoacervate material. Optionally, additional o-rings, c-rings or oval-rings may be included through out the center of the tube to provide additional stability. Such embodiments may be also utilized as vessel grafts. An embodiment of such a vessel graft is depicted in FIG. 17. Normally, in such an embodiment a section of vessel 58 has been removed thereby leaving two open ends 60 and 62. The o-ring 46 or c-ring (not shown) on one end of a tube 64 is then partially inserted into the first opening 60 of the vessel 58 and secured into place by securing means 66 such as sutures or adhesives. Next the o-ring 46 or c-ring (not shown) on the other end of the tube 64 is partially inserted into the other opening 62 of the vessel 58 and sutured into place. Optionally, to minimize the amount of vessel graft inside the lumen the ends of the tube 64 may be narrowed and/or thinned to smooth the transition to and from the vessel to the vessel graft or vessel graft to the vessel.

Figure 18:
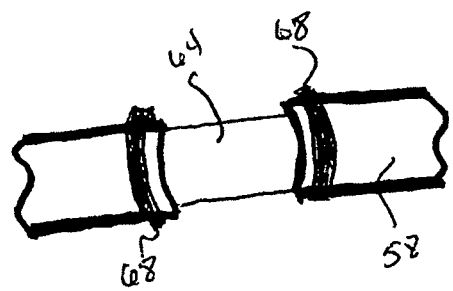
FIG. 18 is a perspective view of one embodiment of a vessel graft including an c-ring at each end of the graft and further including graft fasteners.
Figure 19:
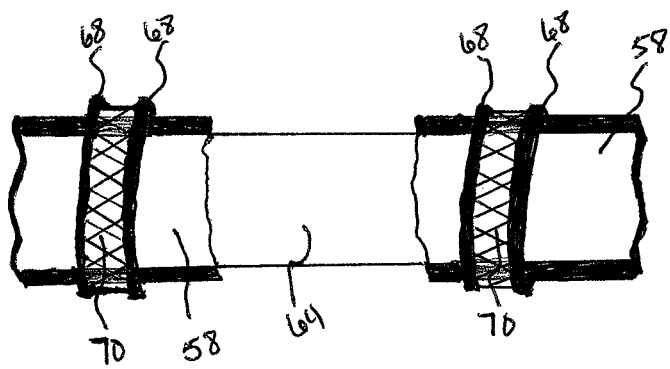
FIG. 19 is a side view of one embodiment of a vessel graft including a graft fastener.

Another vessel graft embodiment may also include graft fasteners to provide strength the anastomosis site and as an aid to wound healing. FIG. 18 depicts one embodiment of the graft fasteners 68 securing the vessel graft 64 to the vessel 58. In various embodiments, the graft fastener 68 may be one or more o-rings, c-rings or oval-rings as described above. However, the fastener 68 may utilize other clamping means suitable for securing the graft 64 to the vessel 58. In one embodiment, depicted in FIG. 19, the graft fasteners 68 includes two or more o-rings, c-rings or oval-rings adjoined by a linking member 70. The linking member 70 may include any type of material, mesh or cloth, such as PTFE, polypropylene, cotton, silk, metal meshing, polyester and the like. In another embodiment the graft fastener may include a self expanding mesh without the o-rings, c-rings or oval-rings, made from similar materials as those identified above. Such a mesh fastener would be able to contract with the exertion of force and return to its original expanded position upon release of the force. The o-rings, c-rings, oval-rings and/or linking member may also be encapsulated or coated with the protein-based material described above to enhance their biocompatibility.

Figure 15:
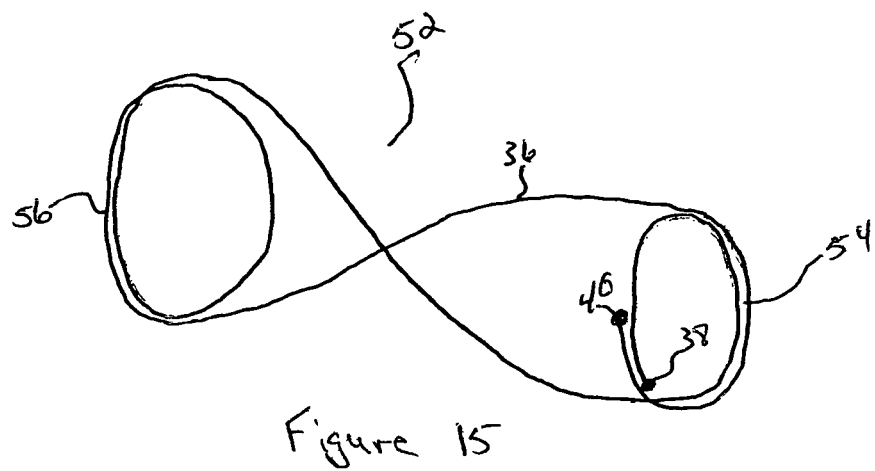
FIG. 15 is a side view of one embodiment of a single strand stent that has a loop strut configuration.

Additionally, as depicted in FIG. 15 another embodiment of a single strand stent may be a loop strut stent 52 that comprises an open or closed loop of a single strand 36, which includes distal and proximal ends 38, 40. The single strand 36 generally takes a half turn at a first loop portion 54 and continues to extend to a second loop portion 56 whereby it takes one and a half turns to form a loop and finally returns to the first loop portion 54 whereby it takes another full turn to complete the loop of the first loop portion. It is again noted that the distal and proximal ends 38, 40 may be adjoined to form a continuous strand.

Figure 16:
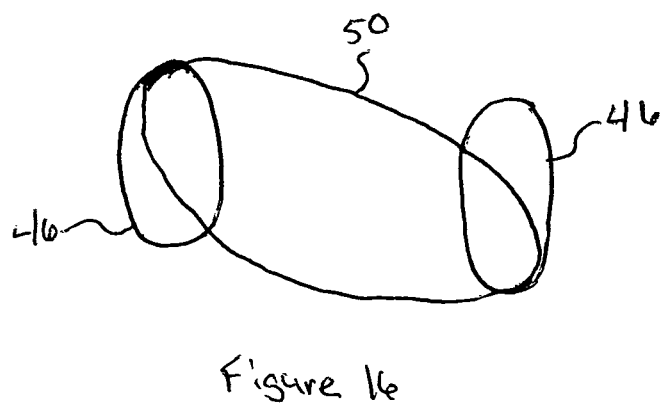
FIG. 16 is a side view of one embodiment of a stent system that has multiple single strand stents including two o-rings and an oval-ring.

It is noted that any of the above mentioned single strand stents may be utilized as a single, as multiples or in combination with other single strand stents to form the stent systems of the present invention. For example, FIG. 16 depicts a stent embodiment that includes multiple o-rings 46 adjoined to a single oval-ring 50. The o-rings 46 are adjoined to the oval-ring 50 by affixing one end of the oval-ring 50 to the top of one o-ring 46 and the opposite end of the oval ring 50 to the bottom of the other o-ring.

The loop struts, as depicted in FIGS. 15 and 16, will allow for much greater blood vessel flexibility than a standard wire stent so that it can change its shape and stretch in response to blood circulation pressure. Here the loop strut is made so that it can collapse on its side and/or elongate to reduce its size so as to fit within a delivery catheter.

It is noted that the single strand stents disclosed above will generally be completely encapsulated within a tube structure of protein matrix material an/or biocoacervate material. However, it is also noted that these stents may also be simple coated with the protein-based materials. The single stranded stents can be reduced in size so that it fits within a catheter assembly without the use of a balloon to deploy it. Also, the single stranded stents can be reduced in size to fit within a delivery catheter that only needs to be freed from the catheter. After protein encapsulated single strand stent is freed from the catheter it will open with greater force than a protein-based material tube without the stent. Furthermore, the encapsulated or coated single stranded stent will add greater force against the vessel wall to hold the stent system in place. It is noted that the single strand stent embodiments may also be coated, surrounded or encapsulated with any suitable biocompatible material that may or may not include a pharmacologically active agent.

Finally, embodiments of the present invention comprise stent systems that include two or more stents coated, separated or encapsulated with one or more of the protein-based materials described above. In various embodiments, the stents are generally configured so that one may be fit within the other or so that they smoothly integrate with each other. As previously suggested, one or more of the stents may be coated or encapsulated with one or more of the protein based materials described above. In various embodiments this may provide the benefit of having a biocompatible material that functions well on the exterior of the stent system may be accomplished by positioning a coating that is biocompatible with the contacting host tissue on the outer stent. Furthermore, a different biocompatible material that functions well on the interior of the stent system may be administered to the inner stent. The insertion of the inner stent into the outer stent may then provide a stent system that functions well with the host tissue on the outside and the material that is present in the lumen.

Alternatively, the stents may simply be separated by a protein-base material. For example, the stent system of the present invention may include multiple stents that have a protein matrix tube positioned between the stents. Such an action may also be accomplished by encapsulating or coating one of the stents and either inserting it into or over a second stent.

It is noted that the following are only examples and therefore any of the protein-based materials and stents may be utilized in the present invention. An example of one embodiment of the invention includes a tube including a protein matrix material that is prepared with collagen:elastin (4:1) with 5% heparin, 0.2 mm thick. The tube is fitted between two stents. The tube length is made to fit the length of the longest stent. The protein matrix material tube is made with a diameter to fit over the inside stent in the closed position and within the outside stent in the closed position. The two stents can then be opened during balloon angioplasty so that the protein matrix material remains between the two stents.

In another example, the protein matrix material may be prepared with collagen:elastin (4:1) with 5% heparin, 0.2 mm thick, and is used to make a tube that fits in between two stents where one or both of the stents are covered in non-protein matrix material. The tube length is made to fit the length of the longest stent. The protein matrix material tube is made with a diameter to fit over the inside stent in the closed position and within the outside stent in the closed position. The two stents can then be opened during balloon angioplasty so that the protein matrix material remains between the two stents. The protein matrix material is positioned so that it comes in contact with the vessel lumen and optionally with the vessel wall (e.g., contact with plaque on vessel wall and/or vessel tissue).

Also in an additional example, the protein matrix material is prepared with collagen:elastin (4:1) with 5% heparin, 0.2 mm thick, and used to make a covering for an ePTFE covered stent by encapsulating the ePTFE covered stent within the protein matrix material in the shape of a tube that fits around the entire ePTFE covered stent.

In another example the protein matrix material covers over an ePTFE covered stent described previously and is used in conjunction with another stent so as to help with deployment of the stent assembly. Generally, the second stent may be placed inside the protein matrix material covered-ePTFE covered stent and pressed against the interior surface of the protein matrix material covered-ePTFE covered stent. The two stents are deployed using various means but the inner stent may aid in gripping the delivery catheter.

EXAMPLES

The biomaterials and biocoacervates of the present invention will now be further described with reference to the following non-limiting examples and the following materials and methods that were employed.

Example 1

Preparation of Biocoacervate

Soluble bovine collagen (Kensey-Nash Corporation) (1.5 gs) was dissolved in distilled water (100 mls) at 42° C. To this solution was added elastin (bovine neck ligament, 0.40 g) and sodium heparinate (0.20g) dissolved in distilled water (40 mls) at room temperature. The elastin/heparin solution was added quickly to the collagen solution with minimal stirring thereby producing an amorphous coacervate precipitate. The resulting cloudy mixture was let stand at room temperature for 1-2 hrs and then refrigerated at 42° F. until the reaction mixture temperature was approximately 20° F. The rubbery precipitate on the bottom of the reaction flask was rinsed three times with fresh distilled water and removed and patted dry with filter paper to yield 6.48 gs of crude coacervate (Melgel) which was then melted at 55° C. and gently mixed to yield a uniform, rubbery, water-insoluble final product after cooling to room temperature. The supernatant of the reaction mixture was later dried down to a solid which weighed 0.417 g and was water soluble.

While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations, which fall within the spirit and broad scope of the invention.

The invention claimed is:

1. A single strand stent system comprising;
one or more single strand stent(s), each stent having at least one single strand twisted to form one or more open loops, the one or more open loops configured to be positioned around the lumen or passageway of a vessel, the at least one single strand including blunt distal and proximal ends, the at least one single strand further coated or encapsulated with a protein based material, the protein based material formed by a process including crosslinking a thermoplastic biocoacervate material that is administered to the one or more single strand stent(s); the thermoplastic biocoacervate material formed by a process including:
adding one or more glycosaminoglycan(s) to a solution of one or more soluble or solubilized primary protein(s), wherein at least one of the one or more primary protein(s) is dissolved in one or more solvent(s) and includes collagen;
minimally mixing the one or more glycosaminoglycan(s) with the one or more primary protein(s) and one or more solvent(s) to precipitate an amorphous coacervate that falls out of the solution as a protein body;
extracting the protein body from the solution and forming the protein body into the thermoplastic biocoacervate material.

2. The single strand stent system of claim 1 further comprising a tube including the protein-based material and wherein the at least one single strand comprises at least two single strands twisted to form two separate loops, each loop coated or encapsulated with the protein-based material, wherein one loop is positioned on an end of the tube and another loop is positioned on the opposite end of the tube.

3. The single strand stent system of claim 2 wherein the tube includes a mesh or cloth coated or encapsulated with the protein based material.

4. The single strand stent system of claim 1 wherein the thermoplastic biocoacervate material includes the one or more primary proteins, the one or more glycosaminoglycans, the one or more solvents and further includes one or more secondary proteins.

5. The single strand stent system of claim 1 wherein the protein based material comprises one or more additional proteins selected from the group consisting of elastin, albumin, keratin, fibronectin, silk, silk fibroin, actin, myosin, fibrinogen, thrombin, aprotinin, antithrombin III, elastinlike blocks, silklike blocks, collagenlike blocks, lamininlike blocks, fibronectinlike blocks, combinations of silklike blocks and elastinlike blocks, collagen-heparin and collagen-chondroitin.

6. The single strand stent system of claim 1 wherein the one or more solvents is water.

7. The single strand stent system of claim 1 further comprising one or more pharmacologically active agents.

8. The single strand stent system of claim 7 wherein the one or more pharmacologically active agents is paclitaxel, rapamycin or estradiol.

9. The single strand stent system of claim 1 wherein the one or more open loops have a shape or configuration selected from the group consisting of a single helix, "o", "c", "e", oval, figure eight and loop strut stent.

10. A vessel graft fastener comprising;
one or more clamping devices adjoined by a linking member including a cloth or mesh material; the one or more clamping devices and linking member coated or encapsulated with a protein-based material formed by administering a thermoplastic biocoacervate material to the one or more clamping devices and the liking member and crosslinking the thermoplastic biocoacervate material to set the thermoplastic biocoacervate material, the biocoacervate is formed by a process including:
adding one or more glycosaminoglycan(s) to a solution of one or more soluble or solubilized primary protein(s) that are dissolved in one or more solvent(s), wherein at least one of the primary protein(s) includes collagen;
minimally mixing the glycosaminoglycan(s) with the primary protein(s) and one or more solvent(s) to precipitate an amorphous coacervate that falls out of the solution as a protein body;
extracting the protein body from the solution, and;
forming the protein body into the thermoplastic biocoacervate.

11. The graft fastener of claim 10 wherein the biocoacervate material includes the one or more primary proteins, the one or more glycosaminoglycans, the one or more solvents and further, one or more secondary proteins.

12. The graft fastener of claim 10 wherein the protein based material comprises one or more additional proteins selected from the group consisting of elastin, albumin, keratin, fibronectin, silk, silk fibroin, actin, myosin, fibrinogen, thrombin, aprotinin, antithrombin III, elastinlike blocks, silklike blocks, collagenlike blocks, lamininlike blocks, fibronectinlike blocks, combinations of silklike blocks and elastinlike blocks, collagen-heparin and collagen-chondroitin.

13. The graft fastener of claim 10 wherein the one or more solvents is water.

14. The graft fastener of claim 10 further comprising one or more pharmacologically active agents.

15. The graft fastener of claim 14 wherein the one or more pharmacologically active agents is paclitaxel, rapamycin or estradiol.

16. The graft fastener of claim 10 wherein the clamping devices are selected from the group consisting of o-rings, c-rings and oval-rings.

17. A stent system comprising:
two or more metallic or polymeric stents that are capable of being integrated one stent within another stent; and a biomaterial coating coated or encapsulated on one or more of the stents and formed by applying a thermoplastic amorphous biocoacervate to the one or more stents, the biocoacervate including one or more soluble or solubilized primary proteins, one or more secondary proteins, one or more glycosaminoglycans(s), and one or more biocompatible solvents, the biomaterial is formed by a process including:
adding the one or more glycosaminoglycan(s) to a solution of one or more of the primary protein(s) that are dissolved in the one or more biocompatible solvents, wherein at least one of the primary protein(s) includes collagen;
minimally mixing the glycosaminoglycan(s) with the one or more primary and secondary protein(s) and one or more solvent(s) to precipitate an amorphous coacervate that falls out of the solution as a protein body;
forming the protein body into the thermoplastic amorphous biocoacervate, and;
crosslinking the biocoacervate with one or more crosslinking agents to form the biomaterial.

18. The stent system of claim 17 wherein the biomaterial coating comprises one or more additional proteins selected from the group consisting of elastin, albumin, keratin, fibronectin, silk, silk fibroin, actin, myosin, fibrinogen, thrombin, aprotinin, antithrombin III, elastinlike blocks, silklike blocks, collagenlike blocks, lamininlike blocks, fibronectinlike blocks, combinations of silklike blocks and elastinlike blocks, collagen-heparin and collagen-chondroitin.

19. The stent system of claim 17 wherein the biocompatible solvent is water.

20. The stent system of claim 17 further comprising one or more pharmacologically active agents.

21. The stent system of claim 20 wherein the one or more pharmacologically active agents is paclitaxel, rapamycin or estradiol.

22. A stent system comprising:
two or more metallic or polymeric stents including an inner stent fitted within one or more outer stents; and first and second protein based materials coating or encapsulating two or more of the two or more stents, the first and/or second protein based materials including a crosslinked biomaterial that is formed by a process including:
adding one or more glycosaminoglycan(s) to a solution of one or more soluble or solubilized primary protein(s) that are dissolved in one or more solvent(s), wherein at least one of the one or more primary protein(s) includes collagen;
minimally mixing the one or more glycosaminoglycan(s) with the one or more primary protein(s) and the one or more solvent(s) to precipitate an amorphous coacervate that falls out of the solution as a protein body;
extracting and forming the protein body into a thermoplastic amorphous biocoacervate, and;
crosslinking the thermoplastic amorphous biocoacervate,
wherein the first protein based material is encapsulated or coated on the inner stent and is biocompatible with host material present in a host lumen, wherein the second protein based material is encapsulated or coated on one or more of the outer stents and is different from the first protein-based material, and wherein the second protein based material is configured to be biocompatible when in contact with host tissue positioned adjacent to the one or more outer stents.

23. The stent system of claim 22 wherein the first protein-based material and second protein-based material are different biomaterials, both protein based materials comprising the one or more primary proteins, the one or more secondary proteins, the one or more glycosaminoglycans and the one or more solvents.

24. The stent system of claim 22 wherein one or both of the first or second protein based materials include one or more proteins selected from the group consisting of elastin, albumin, keratin, fibronectin, silk, silk fibroin, actin, myosin, fibrinogen, thrombin, aprotinin, antithrombin III, elastinlike blocks, silklike blocks, collagenlike blocks, lamininlike blocks, fibronectinlike blocks, combinations of silklike blocks and elastinlike blocks, collagen-heparin and collagen-chondroitin.

25. The stent system of claim 22 wherein the one or more solvents is water.

26. The stent system of claim 22 further comprising one or more pharmacologically active agents.

27. The stent system of claim 26 wherein the one or more pharmacologically active agents is paclitaxel, rapamycin or estradiol.

* * * * *

SEQUENCE LISTING

<160> NUMBER OF SEQ ID NOS: 21

<210> SEQ ID NO 1
<211> LENGTH: 59
<212> TYPE: PRT
<213> ORGANISM: Artificial
<220> FEATURE:
<223> OTHER INFORMATION: synthetic construct similar to silk protein

<400> SEQUENCE: 1

Gly Ala Gly Ala Gly Ser Gly Ala Gly Ala Gly Ser Gly Ala Gly Ala
1               5                   10                  15

Gly Ser Gly Ala Gly Ala Gly Ser Gly Ala Gly Ala Gly Ser Gly Ala
            20                  25                  30

Gly Ala Gly Ser Gly Ala Gly Ala Gly Ser Gly Ala Gly Ala Gly Ser
        35                  40                  45

Gly Ala Gly Ala Gly Ser Gly Ala Ala Gly Tyr
    50                  55

<210> SEQ ID NO 2
<211> LENGTH: 6
<212> TYPE: PRT
<213> ORGANISM: Artificial
<220> FEATURE:
<223> OTHER INFORMATION: seq. repeated indefinitely, synthetic construct
      similar to silk protein

<400> SEQUENCE: 2

Gly Ala Gly Ala Gly Ser
1               5

<210> SEQ ID NO 3
<211> LENGTH: 71
<212> TYPE: PRT
<213> ORGANISM: Artificial
<220> FEATURE:
<223> OTHER INFORMATION: seq. repeated indefinitely, synthetic construct
      similar to silk protein containing RGD sequence from fibronectin.

<400> SEQUENCE: 3

Gly Ala Gly Ala Gly Ser Gly Ala Gly Ala Gly Ser Gly Ala Gly Ala
1               5                   10                  15

Gly Ser Gly Ala Gly Ala Gly Ser Gly Ala Gly Ala Gly Ser Gly Ala
            20                  25                  30

Gly Ala Gly Ser Gly Ala Gly Ala Gly Ser Gly Ala Gly Ala Gly Ser
        35                  40                  45

Gly Ala Gly Ala Gly Ser Gly Ala Ala Val Thr Gly Arg Gly Asp Ser
    50                  55                  60

Pro Ala Ser Ala Ala Gly Tyr
65                  70

<210> SEQ ID NO 4
<211> LENGTH: 74
<212> TYPE: PRT
<213> ORGANISM: Artificial
<220> FEATURE:
<223> OTHER INFORMATION: seq. repeated indefinitely, synthetic construct
      similar to silk protein containing sequence from laminin protein.

<400> SEQUENCE: 4

Gly Ala Gly Ala Gly Ser Gly Ala Gly Ala Gly Ser Gly Ala Gly Ala
1               5                   10                  15

```
Gly Ser Gly Ala Gly Ala Gly Ser Gly Ala Gly Ala Gly Ser Gly Ala
            20                  25                  30

Gly Ala Gly Ser Gly Ala Gly Ala Gly Ser Gly Ala Gly Ala Gly Ser
            35                  40                  45

Gly Ala Gly Ala Gly Ser Gly Ala Ala Pro Gly Ala Ser Ile Lys Val
        50                  55                  60

Ala Val Ser Ala Gly Pro Ser Ala Gly Tyr
65                  70

<210> SEQ ID NO 5
<211> LENGTH: 73
<212> TYPE: PRT
<213> ORGANISM: Artificial
<220> FEATURE:
<223> OTHER INFORMATION: seq. repeated indefinitely, synthetic construct
      similar to silk protein containing a different sequence from
      laminin protein.

<400> SEQUENCE: 5

Gly Ala Gly Ala Gly Ser Gly Ala Gly Ala Gly Ser Gly Ala Gly Ala
1               5                   10                  15

Gly Ser Gly Ala Gly Ala Gly Ser Gly Ala Gly Ala Gly Ser Gly Ala
            20                  25                  30

Gly Ala Gly Ser Gly Ala Gly Ala Gly Ser Gly Ala Gly Ala Gly Ser
        35                  40                  45

Gly Ala Gly Ala Gly Ser Gly Ala Ala Pro Gly Ala Ser Ile Lys Val
    50                  55                  60

Ala Val Ser Gly Pro Ser Ala Gly Tyr
65                  70

<210> SEQ ID NO 6
<211> LENGTH: 71
<212> TYPE: PRT
<213> ORGANISM: Artificial
<220> FEATURE:
<223> OTHER INFORMATION: seq. repeated indefinitely, synthetic construct
      similar to silk protein containing the RGD sequence from
      fibronectin.

<400> SEQUENCE: 6

Gly Ala Gly Ala Gly Ser Gly Ala Gly Ala Gly Ser Gly Ala Gly Ala
1               5                   10                  15

Gly Ser Gly Ala Gly Ala Gly Ser Gly Ala Gly Ala Gly Ser Gly Ala
            20                  25                  30

Gly Ala Gly Ser Gly Ala Gly Ala Gly Ser Gly Ala Gly Ala Gly Ser
        35                  40                  45

Gly Ala Gly Ala Gly Ser Arg Tyr Val Val Leu Pro Arg Pro Val Cys
    50                  55                  60

Phe Glu Lys Ala Ala Gly Tyr
65                  70

<210> SEQ ID NO 7
<211> LENGTH: 20
<212> TYPE: PRT
<213> ORGANISM: Artificial
<220> FEATURE:
<223> OTHER INFORMATION: seq. repeated indefinitely, synthetic construct
      similar to elastin protein.

<400> SEQUENCE: 7

Val Pro Gly Val Gly Val Pro Gly Val Gly Val Pro Gly Val Gly Val
1               5                   10                  15
```

```
Pro Gly Val Gly
            20

<210> SEQ ID NO 8
<211> LENGTH: 52
<212> TYPE: PRT
<213> ORGANISM: Artificial
<220> FEATURE:
<223> OTHER INFORMATION: seq. repeated indefinitely, synthetic construct
      similar to silk and elastin proteins.

<400> SEQUENCE: 8

Gly Val Gly Val Pro Gly Val Gly Val Pro Gly Val Gly Val Pro Gly
1               5                   10                  15

Val Gly Val Pro Gly Val Gly Val Pro Gly Val Gly Val Pro Gly Val
            20                  25                  30

Gly Val Pro Gly Val Gly Val Pro Gly Ala Gly Ala Gly Ser Gly Ala
        35                  40                  45

Gly Ala Gly Ser
    50

<210> SEQ ID NO 9
<211> LENGTH: 82
<212> TYPE: PRT
<213> ORGANISM: Artificial
<220> FEATURE:
<223> OTHER INFORMATION: seq. repeated indefinitely, synthetic construct
      similar to silk and elastin proteins.

<400> SEQUENCE: 9

Gly Ala Ala Val Pro Gly Val Gly Val Pro Gly Val Gly Val Pro Gly
1               5                   10                  15

Val Gly Val Pro Gly Val Gly Val Ala Ala Gly Tyr Gly Ala Gly Ala
            20                  25                  30

Gly Ser Gly Ala Gly Ala Gly Ser Gly Ala Gly Ala Gly Ser Gly Ala
        35                  40                  45

Gly Ala Gly Ser Gly Ala Gly Ala Ser Gly Ala Gly Ala Gly Ser
    50                  55                  60

Gly Ala Gly Ala Gly Ser Gly Ala Gly Ala Gly Ser Gly Ala Gly Ala
65                  70                  75                  80

Gly Ser

<210> SEQ ID NO 10
<211> LENGTH: 111
<212> TYPE: PRT
<213> ORGANISM: Artificial
<220> FEATURE:
<223> OTHER INFORMATION: seq. repeated indefinitely, synthetic construct
      similar to silk and elastin proteins.

<400> SEQUENCE: 10

Gly Ala Gly Ala Gly Ser Gly Ala Gly Ala Gly Ser Gly Ala Gly Ala
1               5                   10                  15

Gly Ser Gly Ala Gly Ala Gly Ser Gly Ala Gly Ala Gly Ser Gly Ala
            20                  25                  30

Gly Ala Gly Ser Gly Ala Ala Gly Tyr Gly Ala Gly Ala Gly Ser Gly
        35                  40                  45

Ala Gly Ala Gly Ser Gly Ala Gly Ala Gly Ser Gly Ala Gly Ala Gly
    50                  55                  60

Ser Gly Ala Gly Ala Gly Ser Gly Val Gly Val Pro Gly Val Gly Val
65                  70                  75                  80
```

-continued

Pro Gly Val Gly Val Pro Gly Val Gly Val Pro
              85                  90                  95

Gly Val Gly Val Pro Gly Val Gly Val Pro Gly Val Gly Val Pro
            100                 105                 110

<210> SEQ ID NO 11
<211> LENGTH: 88
<212> TYPE: PRT
<213> ORGANISM: Artificial
<220> FEATURE:
<223> OTHER INFORMATION: seq. repeated indefinitely, synthetic construct
      similar to silk and elastin proteins.

<400> SEQUENCE: 11

Gly Val Gly Val Pro Gly Val Gly Val Pro Gly Val Gly Val Pro Gly
1               5                   10                  15

Val Gly Val Pro Gly Val Gly Val Pro Gly Val Gly Val Pro Gly Val
            20                  25                  30

Gly Val Pro Gly Val Gly Val Pro Gly Ala Gly Ala Gly Ser Gly Ala
        35                  40                  45

Gly Ala Gly Ser Gly Ala Gly Ala Gly Ser Gly Ala Gly Ala Gly Ser
    50                  55                  60

Gly Ala Gly Ala Gly Ser Gly Ala Gly Ala Gly Ser Gly Ala Gly Ala
65                  70                  75                  80

Gly Ser Gly Ala Gly Ala Gly Ser
                85

<210> SEQ ID NO 12
<211> LENGTH: 108
<212> TYPE: PRT
<213> ORGANISM: Artificial
<220> FEATURE:
<223> OTHER INFORMATION: seq. repeated indefinitely, synthetic construct
      similar to silk and elastin proteins.

<400> SEQUENCE: 12

Gly Val Gly Val Pro Gly Val Gly Val Pro Gly Val Gly Val Pro Gly
1               5                   10                  15

Val Gly Val Pro Gly Val Gly Val Pro Gly Val Gly Val Pro Gly Val
            20                  25                  30

Gly Val Pro Gly Val Gly Val Pro Gly Val Gly Val Pro Gly Val Gly
        35                  40                  45

Val Pro Gly Val Gly Val Pro Gly Val Gly Val Pro Gly Ala Gly Ala
    50                  55                  60

Gly Ser Gly Ala Gly Ala Gly Ser Gly Ala Gly Ala Gly Ser Gly Ala
65                  70                  75                  80

Gly Ala Gly Ser Gly Ala Gly Ala Gly Ser Gly Ala Gly Ala Gly Ser
                85                  90                  95

Gly Ala Gly Ala Gly Ser Gly Ala Gly Ala Gly Ser
            100                 105

<210> SEQ ID NO 13
<211> LENGTH: 128
<212> TYPE: PRT
<213> ORGANISM: Artificial
<220> FEATURE:
<223> OTHER INFORMATION: seq. repeated indefinitely, synthetic construct
      similar to silk and elastin proteins.

<400> SEQUENCE: 13

Gly Val Gly Val Pro Gly Val Gly Val Pro Gly Val Gly Val Pro Gly
1               5                   10                  15

-continued

Val Gly Val Pro Gly Val Gly Val Pro Gly Val Gly Val
          20                  25                  30

Gly Val Pro Gly Val Gly Val Pro Gly Val Gly Val Pro Gly Val Gly
            35                  40                  45

Val Pro Gly Val Gly Val Pro Gly Val Gly Val Pro Gly Val Gly Val
        50                  55                  60

Pro Gly Val Gly Val Pro Gly Val Gly Val Pro Gly Val Gly Val Pro
65                  70                  75                  80

Gly Ala Gly Ala Gly Ser Gly Ala Gly Ala Gly Ser Gly Ala Gly Ala
                85                  90                  95

Gly Ser Gly Ala Gly Ala Gly Ser Gly Ala Gly Ala Gly Ser Gly Ala
            100                 105                 110

Gly Ala Gly Ser Gly Ala Gly Ala Gly Ser Gly Ala Gly Ala Gly Ser
        115                 120                 125

<210> SEQ ID NO 14
<211> LENGTH: 208
<212> TYPE: PRT
<213> ORGANISM: Artificial
<220> FEATURE:
<223> OTHER INFORMATION: seq. repeated indefinitely, synthetic construct
      similar to silk and elastin proteins.

<400> SEQUENCE: 14

Gly Val Gly Val Pro Gly Val Gly Val Pro Gly Val Gly Val Pro Gly
1               5                   10                  15

Val Gly Val Pro Gly Val Gly Val Pro Gly Val Gly Val Pro Gly Val
            20                  25                  30

Gly Val Pro Gly Val Gly Val Pro Gly Val Gly Val Pro Gly Val Gly
        35                  40                  45

Val Pro Gly Val Gly Val Pro Gly Val Gly Val Pro Gly Val Gly Val
    50                  55                  60

Pro Gly Val Gly Val Pro Gly Val Gly Val Pro Gly Val Gly Val Pro
65                  70                  75                  80

Gly Val Gly Val Pro Gly Val Gly Val Pro Gly Val Gly Val Pro Gly
                85                  90                  95

Val Gly Val Pro Gly Val Gly Val Pro Gly Val Gly Val Pro Gly Val
            100                 105                 110

Gly Val Pro Gly Val Gly Val Pro Gly Val Gly Val Pro Gly Val Gly
        115                 120                 125

Val Pro Gly Val Gly Val Pro Gly Val Gly Val Pro Gly Val Gly Val
    130                 135                 140

Pro Gly Val Gly Val Pro Gly Val Gly Val Pro Gly Val Gly Val Pro
145                 150                 155                 160

Gly Ala Gly Ala Gly Ser Gly Ala Gly Ala Gly Ser Gly Ala Gly Ala
                165                 170                 175

Gly Ser Gly Ala Gly Ala Gly Ser Gly Ala Gly Ala Gly Ser Gly Ala
            180                 185                 190

Gly Ala Gly Ser Gly Ala Gly Ala Gly Ser Gly Ala Gly Ala Gly Ser
        195                 200                 205

<210> SEQ ID NO 15
<211> LENGTH: 76
<212> TYPE: PRT
<213> ORGANISM: Artificial
<220> FEATURE:
<223> OTHER INFORMATION: seq. repeated indefinitely, synthetic construct
      similar to silk and elastin proteins.

-continued

<400> SEQUENCE: 15

Gly Val Gly Val Pro Gly Val Gly Val Pro Gly Val Gly Val Pro Gly
1               5                   10                  15

Val Gly Val Pro Gly Val Gly Val Pro Gly Val Gly Val Pro Gly Val
            20                  25                  30

Gly Val Pro Gly Val Gly Val Pro Gly Ala Gly Ala Gly Ser Gly Ala
        35                  40                  45

Gly Ala Gly Ser Gly Ala Gly Ala Gly Ser Gly Ala Gly Ala Gly Ser
    50                  55                  60

Gly Ala Gly Ala Gly Ser Gly Ala Gly Ala Gly Ser
65                  70                  75

<210> SEQ ID NO 16
<211> LENGTH: 64
<212> TYPE: PRT
<213> ORGANISM: Artificial
<220> FEATURE:
<223> OTHER INFORMATION: seq. repeated indefinitely, synthetic construct
      similar to silk and elastin proteins.

<400> SEQUENCE: 16

Gly Val Gly Val Pro Gly Val Gly Val Pro Gly Val Gly Val Pro Gly
1               5                   10                  15

Val Gly Val Pro Gly Val Gly Val Pro Gly Val Gly Val Pro Gly Val
            20                  25                  30

Gly Val Pro Gly Val Gly Val Pro Gly Ala Gly Ala Gly Ser Gly Ala
        35                  40                  45

Gly Ala Gly Ser Gly Ala Gly Ala Gly Ser Gly Ala Gly Ala Gly Ser
    50                  55                  60

<210> SEQ ID NO 17
<211> LENGTH: 56
<212> TYPE: PRT
<213> ORGANISM: Artificial
<220> FEATURE:
<223> OTHER INFORMATION: seq. repeated indefinitely, synthetic construct
      similar to keratin protein.

<400> SEQUENCE: 17

Ala Lys Leu Lys Leu Ala Glu Ala Lys Leu Glu Leu Ala Glu Ala Lys
1               5                   10                  15

Leu Lys Leu Ala Glu Ala Lys Leu Glu Leu Ala Glu Ala Lys Leu Lys
            20                  25                  30

Leu Ala Glu Ala Lys Leu Glu Leu Ala Glu Ala Lys Leu Lys Leu Ala
        35                  40                  45

Glu Ala Lys Leu Glu Leu Ala Glu
    50                  55

<210> SEQ ID NO 18
<211> LENGTH: 15
<212> TYPE: PRT
<213> ORGANISM: Artificial
<220> FEATURE:
<223> OTHER INFORMATION: seq. repeated indefinitely, synthetic construct
      similar to collagen protein.

<400> SEQUENCE: 18

Gly Ala Pro Gly Pro Pro Gly Pro Gly Pro Pro Gly Pro Pro
1               5                   10                  15

<210> SEQ ID NO 19

```
<211> LENGTH: 39
<212> TYPE: PRT
<213> ORGANISM: Artificial
<220> FEATURE:
<223> OTHER INFORMATION: seq. repeated indefinitely, synthetic construct
      similar to collagen protein.

<400> SEQUENCE: 19

Gly Ala Pro Gly Pro Pro Gly Pro Pro Gly Pro Pro Gly Pro Pro Gly
1               5                   10                  15

Ala Pro Gly Pro Pro Gly Pro Pro Gly Pro Pro Gly Pro Pro Gly Pro
            20                  25                  30

Ala Gly Pro Val Gly Ser Pro
        35

<210> SEQ ID NO 20
<211> LENGTH: 63
<212> TYPE: PRT
<213> ORGANISM: Artificial
<220> FEATURE:
<223> OTHER INFORMATION: seq. repeated indefinitely, synthetic construct
      similar to collagen protein with a cell binding domain from human
      collagen.

<400> SEQUENCE: 20

Gly Ala Pro Gly Pro Pro Gly Pro Pro Gly Pro Pro Gly Pro Pro Gly
1               5                   10                  15

Ala Pro Gly Pro Pro Gly Pro Pro Gly Pro Pro Gly Pro Pro Gly Leu
            20                  25                  30

Pro Gly Pro Lys Gly Asp Arg Gly Asp Ala Gly Pro Lys Gly Ala Asp
        35                  40                  45

Gly Ser Pro Gly Pro Ala Gly Pro Ala Gly Pro Val Gly Ser Pro
    50                  55                  60

<210> SEQ ID NO 21
<211> LENGTH: 15
<212> TYPE: PRT
<213> ORGANISM: Artificial
<220> FEATURE:
<223> OTHER INFORMATION: seq. repeated indefinitely, synthetic construct
      similar to collagen protein.

<400> SEQUENCE: 21

Gly Ala Pro Gly Ala Pro Gly Ser Gln Gly Ala Pro Gly Leu Gln
1               5                   10                  15
```